US006960611B2

(12) United States Patent
Guo et al.

(10) Patent No.: US 6,960,611 B2
(45) Date of Patent: Nov. 1, 2005

(54) SULFONYL-CONTAINING 2,3-DIARYLINDOLE COMPOUNDS, METHODS FOR MAKING SAME, AND METHODS OF USE THEREOF

(75) Inventors: Zongru Guo, Beijing (CN); Guifang Cheng, Beijing (CN); Fengming Chu, Beijing (CN); Wen Hui Hu, Beijing (CN); Zhi Bin Xu, Beijing (CN); Ai Ping Bai, Beijing (CN)

(73) Assignee: Institute of Materia Medica, Beijing (CN)

( * ) Notice: Subject to any disclaimer, the term of this patent is extended or adjusted under 35 U.S.C. 154(b) by 0 days.

(21) Appl. No.: 10/243,957

(22) Filed: Sep. 16, 2002

(65) Prior Publication Data

US 2004/0058977 A1 Mar. 25, 2004

(51) Int. Cl.$^7$ ..................... A61K 31/404; C07D 209/04
(52) U.S. Cl. ........................ 514/415; 548/490; 548/491
(58) Field of Search ................................ 548/490, 491, 548/511; 514/415

(56) References Cited

U.S. PATENT DOCUMENTS

| | | | |
|---|---|---|---|
| 3,551,451 A | * 12/1970 | Szmuszkovicz et al. .... 548/511 |
| 3,905,999 A | 9/1975 | Krutak et al. |
| 4,233,299 A | 11/1980 | Trummlitz et al. |
| 5,521,213 A | 5/1996 | Prasit et al. |
| 5,684,020 A | 11/1997 | Peglion et al. |
| 5,872,189 A | 2/1999 | Bett et al. |
| 6,329,421 B1 | 12/2001 | Prasit et al. |

FOREIGN PATENT DOCUMENTS

| | | |
|---|---|---|
| DE | 27 56 113 | 12/1977 |
| EP | 0 745 598 | 12/1996 |
| EP | 0 961 204 | 12/1999 |
| WO | 96/13483 | 5/1996 |
| WO | 96/41825 | 12/1996 |
| WO | 97/30030 | 8/1997 |

OTHER PUBLICATIONS

Dann et al (1975): STN International CAPLUS database, (Columbus, Ohio), Accession No.: 1975: 156162.*
Hu et al. (2002): STN International CAPLUS Database (Columbus, Ohio), document No. 137:262918. In Chinese Chemical Letters (2002), 13 (40, 296–298.*

* cited by examiner

*Primary Examiner*—Golam M. M. Shameem
(74) *Attorney, Agent, or Firm*—Nixon & Vanderhye P.C.

(57) ABSTRACT

The present invention relates to sulfonyl-containing 2,3-diarylindole, especially to new compounds of general Formula, to a preparation method for their preparation, to pharmaceutical compositions containing said compound, and to the medical use thereof in the treatment of diseases relating to the inhibition of cyclooxygenase-2 (COX-2).

18 Claims, No Drawings

SULFONYL-CONTAINING 2,3-DIARYLINDOLE COMPOUNDS, METHODS FOR MAKING SAME, AND METHODS OF USE THEREOF

FIELD OF THE INVENTION

The present invention generally relates to novel sulfonyl-containing 2,3-diarylindole compounds that selectively inhibit cyclooxygenase-2 (COX-2), pharmaceutical compositions containing such compounds, methods for preparing such compounds and methods for using these compounds, alone or in combination with other therapeutic agents, for the treatment or prevention of symptoms or manifestations associated with diseases or disorders affected or regulated by COX-2.

BACKGROUND OF THE INVENTION

Non-steroidal anti-inflammatory drugs (NSAIDs) are compounds used extensively for the treatment of inflammatory conditions, including pain-releasing, anti-pyretic and rheumatoid arthritis. The combined analgesic and anti-inflammatory effects of NSAIDs make them particularly useful for the symptomatic relief of painful and/or inflammatory conditions including musculoskeletal and joint disorders, such as rheumatoid arthritis, osteoarthritis, spondylo arthopathic, peri-articular and soft tissue disorder. NSAIDs are believed to inhibit the enzyme cyclooxygenase (COX) that is involved in the biosynthesis of prostaglandins G and H from arachidonic acid. Prostaglandins (PGs) are ubiquitous fatty acid derivatives that serve as autocrine/paracrine mediators involved in many different physiological processes in addition to their well recognized role in inflammation and immune response modulation. Prostaglandins elicit a variety of important and beneficial responses. Among the undesirable properties of Prostaglandins is their ability to induce pain, fever, and symptoms associated with the inflammatory response. NSAIDS exert their actions primarily by inhibiting the production of PGs. Recent studies of inflammatory processes has led to the identification of the key enzyme COX that is expressed in inflammatory conditions. So far two isozymes of COX are known: COX-1 and COX-2. COX-1 is constitutively produced in a variety of tissues and appears to be important to the maintenance of normal physiological functions, including gastric and renal cytoprotection. COX-2 is an inducible isozyme, which is produced in cells under the stimulation of endotoxins, cytokines, and hormones and catalyzes or regulates the production of prostaglandins which cause inflammation. The prostaglandins synthesized by COX-2 are mediators of inflammation, the body's response to injury characterized by increased blood flow to the tissue, increased temperature, redness, accumulation of immune cells and pain. COX-2 and prostaglandins are also involved in the spread of tumors, such as in colon cancer. COX-2 is over-expressed in colon cancer tissue. COX-2 inhibitors possess potential prophylactic and therapeutic application to colon cancer. They reduce the rate of cell death, increase the invasiveness of the malignancies and promote the growth of blood vessels that deliver nourishment to the lesions. Currently, drugs that inhibit COX-2 are prescribed in the treatment of pre-cancerous polyps in the colon and colon cancer, where cells have increased levels of the enzyme. Moreover, it has been shown that an inflammatory process in brain cells may contribute to Alzheimer's disease (AD) damage and that several compounds and processes known to be involved in inflammation can be found in and around AD plaques (dense, insoluble protein deposits that are found outside and around the brain's nerve cells and are associated with AD). If these processes contribute to the death of neurons, it has been proposed that suppressing the inflammatory activity, by using NSAIDs, should slow the rate of progression of AD.

The current therapeutic use of NSAIDs, however, has been associated with the inhibition of both COX-1 and COX-2 and causes well-known side effects at the gastrointestinal and renal level. Therefore, the selective COX-2 inhibitors could provide anti-inflammatory agents devoid of the undesirable effects associated with classical, nonselective NSAIDs. Previous NSAIDs have been found to prevent the production of prostaglandins by inhibiting enzymes in the human arachidonic acid/prostaglandin pathway, including the enzyme cyclooxygenase. The discovery of an inducible enzyme associated with inflammation COX-2 or "prostaglandin G/H synthase II" has provided a viable target of inhibition which more effectively reduces inflammation and produces fewer and less drastic side effects related to inhibition of COX-1. The COX-2 inhibitors as selective anti-inflammatory drugs are chemically aminosulfonylaryl or methylsulfonylaryl-containing substances, such as Nimesulide (R. H. Brogen and A. Ward. Drugs, 1998, 36: 732–753), NS-398 (JP 1990000268, JP 1990300122), Meloxicom (DE 2756113), pyrrazole-containing tricyclic compounds, for example, Celecoxib (WO 96/41825, WO 96/41626), oxazole-containing tricyclic compounds, for example, JRE-522 (EP 0745596), unsaturated gamma-lactone-containing compounds, for example, Rofecoxib (EP 0788476). The non-selective NSAID Indomethacin as a lead compound was chemically modified to give rise to selective COX-2 inhibitors without sulfonyl groups, for example L-748780 and L-761066 (W. C. Black et al. Bioorg Med. Chem. Lett. 1996, 6: 725–742,). These compounds exhibit selective COX-2 inhibition activity at differing levels and constitute a group of anti-inflammatory drugs with little adverse reactions. However, a need still exists for novel compounds, pharmaceutical compositions and methods for effectively inhibiting COX-2.

SUMMARY OF THE INVENTION

It is an object of the present invention to provide novel therapeutic compounds, and methods for making same, that are stable and/or metabolically stable, including pharmaceutical compositions thereof and methods useful for selectively inhibiting COX-2.

It is a further object of the present invention to provide novel therapeutic compounds, pharmaceutical compositions thereof and methods that are capable of treating or preventing disease or conditions mediated by or related to COX-2.

One or more of the above and other objects are accomplished by sulfonyl-containing 2,3-diarylindole compounds, including pharmaceutically acceptable derivatives (e.g., pharmaceutically acceptable racemic mixtures, resolved enantiomers, diastereomers, tautomers, salts and solvates thereof) or prodrugs thereof, having the following Formula I:

(I)

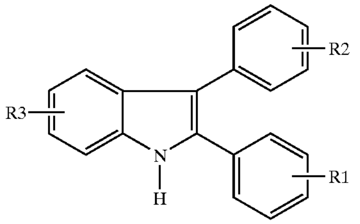

wherein $R_1$, $R_2$ and $R_3$ are defined herein. Without wishing to be bound by theory, it is believed that the therapeutic compounds of the present invention act by selectively inhibiting COX-2.

In another aspect, the present invention provides methods of preparing the compounds of sulfonyl-containing 2,3-diarylindole.

An additional aspect the present invention is to provide pharmaceutical compositions which comprise a therapeutically effective amount of one or more of the compounds of Formula I, as described herein, Formulated together with one or more pharmaceutically acceptable carriers.

In a further aspect the present invention is to provide methods for using the compounds of Formula I to the diseases relevant to COX-2. In particular, the present invention comprises a method for treating or preventing a COX-2 associated disorder such as inflammation and/or pain associated with inflammation in a subject in need of such treatment or prevention. The method comprising treating the subject having or susceptible to such inflammation or disorder with a therapeutically-effective amount of the compound of Formula I, as further described herein. As such, a skilled artisan will appreciate that compounds of the present invention would be useful for, but not limited to, the treatment of inflammation in a subject, and for treatment of other COX-2 mediated disorders, such as, as an analgesic in the treatment of pain and headaches, or as an antipyretic for the treatment of fever. For example, compounds of the present invention would be useful to treat arthritis, including but not limited to rheumatoid arthritis, spondyloarthropathies, gouty arthritis, osteoarthritis, systemic lupus erythematosus and juvenile arthritis. Compounds of the present invention would be useful in the treatment of asthma, bronchitis, menstrual cramps, preterm labor, tendinitis, bursitis, liver disease including hepatitis, skin-related conditions such as psoriasis, eczema, burns and dermatitis, and from post-operative inflammation including from ophthalmic surgery such as cataract surgery and refractive surgery. Compounds of the present invention also would be useful to treat gastrointestinal conditions such as inflammatory bowel disease, Crohn's disease, gastritis, irritable bowel syndrome and ulcerative colitis. Compounds of the present invention would be useful for the prevention or treatment of cancer, such as colorectal cancer, and cancer of the breast, lung, prostate, bladder, cervix and skin. Compounds of the present invention would be useful in treating glaucoma, angiogenesis and retinopathies. Compounds of the present invention would be useful in treating inflammation in such diseases as vascular diseases including atherosclerosis, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. Compounds of the present invention would also be useful in the treatment of ophthalmic diseases, such as retinitis, conjunctivitis, retinopathies, uveitis, ocular photophobia, and of acute injury to the eye tissue. Compounds of the present invention would also be useful in the treatment of pulmonary inflammation, such as that associated with viral infections and cystic fibrosis. Compounds of the present invention would also be useful for the treatment of certain central nervous system disorders, such as cortical dementias including Alzheimer's disease, and central nervous system damage resulting from stroke, ischemia, seizures and trauma. Compounds of the present invention are useful as antiinflammatory agents, such as for the treatment of arthritis, with the additional benefit of having significantly less harmful side effects. Compounds of the present invention would also be useful in the treatment of allergic rhinitis, respiratory distress syndrome, endotoxin shock syndrome, osteoporosis and inhibiting bone resorption. Compounds of the present invention also would be useful in the treatment of pain, but not limited to postoperative pain, dental pain, muscular pain, and pain resulting from cancer. Compounds of the present invention would be useful for the prevention of cardiovascular disease, such as atherosclerosis, liver disease and dementias, such as Alzheimer's Disease. Besides being useful for human treatment, the present invention is also useful for veterinary treatment of companion animals, exotic animals and farm animals, including mammals, rodents, and the like. More preferred animals include horses, dogs, and cats.

Additional objects and attendant advantages of the present invention will be set forth, in part, in the description that follows, or may be learned from practicing or using the present invention. The objects and advantages may be realized and attained by means of the compounds, compositions and methods pointed out in the appended claims. It is to be understood that the foregoing general description and the following detailed description are exemplary and explanatory only and are not to be viewed as being restrictive of the invention, as claimed.

DESCRIPTION OF PREFERRED EMBODIMENTS

All patents, patent applications and literatures cited in this description are incorporated herein by reference in their entirety. In the case of inconsistencies, the present disclosure, including definitions, will control.

The following definitions are adopted. Some definitions apply to all Formulas presented herein, others apply to only some Formulas presented herein, as will be apparent to a person of skill in the art.

The term "hydrido" denotes a single hydrogen atom (H). This hydrido radical may be attached, for example, to an oxygen atom to form a hydroxyl radical or two hydrido radicals may be attached to a carbon atom to form a methylene (—CH2—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl" embraces linear or branched alkyl radicals having one to about ten carbon atoms any one of which may be substituted with one-or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl.

The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical, that is, to form monoalkoxyalkyl and dialkoxyalkyl radicals. More preferred alkoxyalkyl radicals are "lower alkoxyalkyl" radicals having one to six carbon atoms and one or two alkoxy radicals. Examples of such radicals include methoxymethyl, methoxyethyl, ethoxyethyl methoxybutyl and methoxypropyl. The "alkoxy" or "alkoxyalkyl" radicals may be further substituted with one or more halo atoms, such as fluoro, chloro or bromo, to provide "haloalkoxy" or "haloalkoxyalkyl" radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy.

The term "cyanoalkyl" embraces radicals having a cyano or nitrile (—CN) radical attached to an alkyl radicals as described above. More preferred cyanoalkyl radicals are "lower cyanoalkyl" radicals having one to six carbon atoms. Examples of such lower cyanoalkyl radicals include cyanomethyl, cyanopropyl, cyanoethyl and cyanobutyl.

The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces unsaturated cyclic radicals having three to ten carbon atoms. More preferred cycloalkenyl radicals are "lower cycloalkenyl" radicals having about five to about eight carbon atoms. Examples of such radicals include cyclobutenyl, cyclopentenyl, cyclohexenyl and cycloheptenyl.

The term "aryl", alone or in combination, means a carbocyclic aromatic system containing one, two or three rings wherein such rings may be attached together in a pendent manner or may be fused.

The term "aryl" embraces aromatic radicals such as phenyl, naphthyl, tetrahydronaphthyl, indane and biphenyl.

The terms "heterocyclic" and "heterocyclo" embrace saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole.

The term "heteroaryl" embraces unsaturated heterocyclic radicals. Examples of unsaturated heterocyclic radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3 to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated. condensed heterocyclic group containing 1 to 2 oxygen atoms and. 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like.

The term also embraces radicals where heterocyclic radicals are fused with aryl radicals. Examples of such fused bicyclic radicals include benzofuryl, benzothienyl, and the like. Said "heterocyclic" radicals may have 1 to 3 substituents such as lower alkyl, hydroxy, oxo, amino and lower alkylamino. More preferred heteroaryl radicals include five to six membered heteroaryl radicals.

The term "heterocyclicalkyl" embraces heterocyclic-substituted alkyl radicals. More preferred heterocyclicalkyl radicals are "lower heterocyclicalkyl" radicals having one to six carbon atoms and a heterocyclic radical. Examples include such radicals as pyrrolidinylmethyl.

The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio.

The term "alkylthioalkyl" embraces alkylthio radicals attached to an alkyl radical. More preferred alkylthioalkyl radicals are "lower alkylthioalkyl" radicals having alkyl radicals of one to six carbon atoms and an alkylthio radical as described above. Examples of such radicals include methylthiomethyl.

The term "arylthio" embraces radicals containing an aryl radical, attached to a divalent sulfur atom, such as a phenylthio radical.

The term "arylthioalkyl" embraces arylthio radicals attached to an alkyl radical. More preferred arylthioalkyl radicals are "lower arylthioalkyl" radicals having alkyl radicals of one to six carbon atoms and an arylthio radical as described above. Examples of such radicals include phenylthiomethyl.

The term "alkylsulfinyl" embraces radicals containing a linear or branched alkyl radical, of one to ten carbon atoms, attached to a divalent —S(═O)— radical. More preferred alkylsulfinyl radicals are "lower alkylsulfinyl" radicals having one to six carbon atoms. Examples of such lower alkylsulfinyl radicals include methylsulfinyl, ethylsulfinyl, butylsulfinyl and hexylsulfinyl.

The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide "haloalkylsulfonyl" radicals. More preferred haloalkylsulfonyl radicals are "lower haloalkylsulfonyl" radicals having one or more halo atoms attached to lower alkylsulfonyl radicals as described above. Examples of such lower haloalkylsulfonyl radicals include fluoromethylsulfonyl, trifluoromethylsulfonyl and chloromethylsulfonyl.

The term "arylsulfonyl" embraces aryl radicals as defined above, attached to a sulfonyl radical. Examples of such radicals include phenylsulfonyl.

The term "aralkylsulfonyl" embraces aralkyl radicals as defined above, attached to a sulfonyl radical. Examples of such radicals include benzylsulfonyl.

The term "heteroarylsulfonyl" embraces heteroaryl radicals as defined above, attached to a sulfonyl radical. Examples of such radicals include thienylsulfonyl, oxazolylsulfonyl and pyridylsulfonyl.

The term "heteroarylalkylsulfonyl" embraces heteroarylalkyl radicals as defined above, attached to a sulfonyl radical. Examples of such radicals include thienylmethylsulfonyl.

The terms "sulfamyl", "aminosulfonyl" and "sulfonamidyl" denotes $NH_2O_2S$—.

The term "acyl" denotes a radical provided by the residue after removal of hydroxyl from an organic acid. Examples of such acyl radicals include formyl, alkanoyl and aroyl radicals.

The terms "carboxy" or "carboxyl", whether used alone or with other terms, such as "carboxyalkyl", denotes —$CO_2H$.

The term "carbonyl", whether used alone or with other terms, such as "alkoxycarbonyl", denotes —(C═O)—.

The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl.

The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl.

The aryl in said aralkyl may be additionally substituted with halo, alkyl, alkoxy, haloalkyl and haloalkoxy.

The terms benzyl and phenylmethyl are interchangeable.

The term "aralkenyl" embraces aryl-substituted alkenyl radicals. Preferable aralkenyl radicals are "lower aralkenyl" radicals having aryl radicals attached to alkenyl radicals having two to six carbon atoms. Examples of such radicals include phenylethenyl and diphenylethenyl. The aryl in said aralkenyl may be additionally substituted with halo, alkyl, alkoxy, haloalkyl and haloalkoxy.

The terms "alkylcarbonyl", "arylcarbonyl" and "aralkylcarbonyl" include radicals having alkyl, aryl and aralkyl radicals, respectively, as defined above, attached via an oxygen atom to a carbonyl radical. More preferred alkylcarbonyl radicals are "lower alkylcarbonyl" radicals having one to six carbon atoms. Examples of such radicals include methylcarbonyl and ethylcarbonyl. More preferred aralkylcarbonyl radicals are "lower aralkylcarbonyl" radicals having aryl radicals attached to alkyl radicals having one to six carbon atoms. Examples of such aralkylcarbonyl radicals include benzylcarbonyl. An example of an arylcarbonyl radical is phenylcarbonyl.

The term "alkoxycarbonylalkyl" embraces radicals having "alkoxycarbonyl", as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl.

The term "haloalkylcarbonyl" embraces radicals having a haloalkyl radical as described above attached to a carbonyl radical. More preferred radicals are "lower haloalkylcarbonyl" radicals where lower haloalkyl radicals, as described above are attached to a carbonyl radical.

The term "carboxyalkyl" embrace radicals having a carboxy radical as defined above, attached to an alkyl radical. The alkanoyl radicals may be substituted or unsubstituted, such as formyl, acetyl, propionyl, butyryl, isobutyryl, valeryl, isovaleryl, pivaloyl, hexanoyl, trifluoroacetyl or the like, in which the preferable one is formyl, acetyl, propionyl or trifluoroacetyl.

The term "heteroaralkyl" embraces heteroaryl-substituted alkyl radicals. More preferred heteroaralkyl radicals are "lower heteroaralkyl" radicals having five to six membered heteroaryl radicals attached to one to six carbon atoms. Examples of such radicals include pyridylmethyl, quinolylmethyl, thienylmethyl, furylethyl and quinolylethyl. The heteroaryl in said heteroaralkyl may be additionally substituted with halo, alkyl, alkoxy, haloalkyl and haloalkoxy.

The term "aryloxy" embraces aryl radicals, as defined above, attached to an oxygen atom. The aryl in said aryloxy may be additionally substituted with one or more halo, alkyl, alkoxy, haloalkyl and haloalkoxy radicals. Examples of such radicals include phenoxy.

The term "heteroaryloxy" embraces heteroaryl radicals as defined above attached to an oxygen radical. More preferred heteroaryloxy radicals are "lower heteroaryloxy" radicals having five to six membered heteroaryl radicals.

The term "aralkoxy" embraces oxy-containing aralkyl radicals attached through an oxygen atom to other radicals.

The term "aralkoxyalkyl" embraces alkyl radicals having one or more aralkoxy radicals attached to the alkyl radical, that is, to form monoaralkyloxyalkyl and diaralkyloxyalkyl radicals. The "aralkoxy" or "aralkoxyalkyl" radicals may be further substituted on the aryl ring portion of the radical. More preferred aralkoxyalkyl radicals are "lower aralkoxyalkyl" having an alkoxy attached to one to six carbon atoms. Examples of lower aralkoxyalkyl radicals include benzyloxymethyl.

The term "heteroarylthio" embraces radicals having heteroaryl radicals attached to a sulfur radical. More preferred heteroarylthio radicals are "lower heteroarylthio" radicals having five to six membered heteroaryl radicals. Examples of such radicals include 2-furylthio, 2-thienylthio, 3-thienylthio, 4-pyridylthio and 3-pyridylthio.

The term "alkoxyaralkoxyalkyl" embraces alkoxy substituted aralkoxyalkyl radicals. More preferred radicals have lower alkoxy substituted aralkoxyalkyl, where lower alkoxy is defined above.

The terms "heteroaralkylthio" and "heteroaralkylthio" denote radicals having an heteroaryl radical attached to an alkylthio radical. More preferred heteroaralkylthio radicals are "lower heteroaralkylthio" radicals having heteroaryl radicals attached to lower alkylthio radicals as described above. Examples of such radicals include furylmethylthiomethyl and quinolylmethylthioethyl.

The term "heteroarylalkylthioalkyl" denotes radicals having an heteroaryl radical attached to an alkylthio radical further attached through the sulfur atom to an alkyl radical. More preferred heteroarylalkylthioalkyl are "lower heteroarylalkylthioalkyl" radicals having lower heteroarylalkyl radicals as described above. Examples of such radicals include furylmethylthiomethyl and quinolylmethylthioethyl.

The term "heteroarylthioalkyl" denotes radicals having an heteroaryl radical attached to a sulfur atom further attached through the sulfur atom to an alkyl radical. More preferred heteroarylthioalkyl radicals are "lower heteroarylthioalkyl" having lower heteroarylthio radicals as described above. Examples of such radicals include thienylthiomethyl and pyridylthiohexyl.

The term "aralkylthio" embraces radicals having aralkyl radicals attached to a bridging sulfur atom. More preferred aralkylthio radicals are "lower aralkylthio" radicals having the aryl radicals attached to one to six carbon atoms. Examples of such radicals include benzylthio and phenylethylthio.

The term "aralkylthioalkyl" embraces radicals having aralkyl radicals attached to alkyl radicals through a bridging sulfur atom. More preferred aralkylthioalkyl radicals are "lower aralkylthioalkyl" radicals having the aralkylthio radicals attached to one to six carbon atoms. Examples of such radicals include benzylthiomethyl and phenylethylthiomethyl.

The term "heteroaryloxyalkyl" denotes radicals having an heteroaryl radical attached to an oxygen atom further attached through the oxygen atom to an alkyl radical. More preferred heteroaryloxyalkyl radicals are "lower heteroaryloxyalkyl" radicals having five to six membered heteroaryl radicals. Examples of such radicals include furylbutoxyethyl, pyridyloxymethyl and thienyloxyhexyl.

The term "aminoalkyl" embraces alkyl radicals substituted with amino radicals. More preferred aminoalkyl radicals are "lower aminoalkyl" having one to six carbon atoms. Examples include aminomethyl, aminoethyl and aminobutyl.

The term "alkylaminoalkyl" embraces aminoalkyl radicals having the nitrogen atom substituted with at least one alkyl radical. More preferred alkylaminoalkyl radicals are "lower alkylaminoalkyl" having one to six carbon atoms attached to a lower aminoalkyl radical as described above. More preferred alkylamino radicals are "lower alkylamino" radicals having one or two alkyl radicals of one to six carbon atoms, attached to a nitrogen atom.

The term "alkylamino" denotes amino groups which have been substituted with one or two alkyl radicals. Suitable "alkylamino" may be mono or dialkylamino such as N-methylamino, N-ethylamino, N,N-dimethylamino, N,N-diethylamino or the like.

The term "alkylaminocarbonyl" embraces alkylamino radicals, as described above, to a carbonyl radical. More preferred alkylaminocarbonyl radicals are "lower alkylaminocarbonyl" having lower alkylamino radicals, as described above; attached to a carbonyl radical. Examples of such radicals include N-methylaminocarbonyl and N,N-dimethylcarbonyl.

The term "arylamino" denotes amino groups which have been substituted with one or two aryl radicals, such as N-phenylamino. The "arylamino" radicals may be further substituted on the aryl ring portion of the radical.

The terms "N-arylaminoalkyl" and "N-aryl-N-alkylaminoalkyl" denote amino groups which have been substituted with one aryl radical or one aryl and one alkyl radical, respectively, and having the amino group attached to an alkyl radical. More preferred arylaminoalkyl radicals are "lower arylaminoalkyl" having the arylamino radical attached to one to six carbon atoms. Examples of such radicals include N-phenylaminomethyl and N-phenyl-N-methylaminomethyl.

The term "aminocarbonyl" denotes an amide group of the Formula $—C(=O)NH_2$.

The term "alkylaminocarbonylalkyl" denotes an aminocarbonyl group which has been substituted with one or two alkyl radicals. More preferred are "lower alkylaminocarbonylalkyl" having lower alkylaminocarbonyl radicals as described above attached to one to six carbon atoms.

The term "aryloxyalkyl" embraces alkyl radicals having one or more aryloxy radicals, aryl radicals attached to a divalent oxygen atom, attached to the alkyl radical, that is, to form monoaryloxyalkyl and diaryloxyalkyl radicals. The more preferred aryloxyalkyl radicals are "lower aryloxyalkyl" radicals having aryloxy radicals attached to one to six carbon atoms. Examples include phenoxymethyl.

The terms "heteroaralkoxyalkyl" and "heteroarylalkoxyalkyl" embrace alkyl radicals having one or more heterocyclic radicals attached to an alkoxy radical, further attached to the alkyl radical. More preferred heteroaralkoxyalkyl radicals are "lower heteroaryl alkoxyalkyl radicals having five to six membered heteroaryl radicals. Examples of such radicals include 2-thienylmethoxymethyl.

"Optional" or "optionally" means that the subsequently described event or circumstance may or may not occur, and that the description includes, without limitation, instances where said event or circumstance occurs and instances in which it does not. For example, optionally substituted alkyl means that alkyl may or may not be substituted by those groups enumerated in the definition of substituted alkyl.

"Pharmaceutically acceptable derivative" or "prodrug" means any pharmaceutically acceptable salt, ester, salt of an ester, or other derivative of a compound of the present invention that, upon administration to a recipient, is capable of providing (directly or indirectly) a compound of the present invention. Particularly favored derivatives and prodrugs are those that increase the bioavailability of the compounds of the present invention when such compounds are administered to a mammal (e.g., by allowing an orally administered compound to be more readily absorbed into the blood) or that enhance delivery of the parent compound to a biological compartment (e.g., the brain or lymphatic system) relative to the parent species. Prodrugs are considered to be any covalently bonded carriers which release the active parent drug according to Formula I in vivo when such prodrug is administered to a mammalian subject. Preferred prodrugs include, without limitation, derivatives where a group that enhances aqueous solubility or active transport through the gut membrane is appended to the structure of Formula I. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group, respectively. Examples of prodrugs include, but are not limited to, acetate, formate and benzoate derivatives of alcohol and amine functional groups in the compounds of Formula I, and the like.

"Pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds of Formula I include the conventional nontoxic salts or the quaternary ammonium salts of the compounds of Formula I formed, for example, from nontoxic inorganic or organic acids. In particular, suitable pharmaceutically-acceptable acid addition salts of compounds of Formula I may be prepared from an inorganic acid or from an organic acid. For example, such conventional non-toxic salts include, without limitation, those derived from inorganic acids such as acetic, 2-acetoxybenzoic, 2-naphthalenesulfonilic, adipic, alginic, ascorbic, aspartic, benzoic, benzenesulfonic, bisulfic, butyric, camphoric, camphorsulfonic, carbonic, citric, cyclopentanepropionic, digluconic, dodecylsulfanilic, ethane sulfonilic, ethane disulfonic, fumaric, glucoheptanoic, glutamic, glycerophosphic, glycolic, hemisulfanoic, heptanoic, hexanoic, hydrobromic, hydrochloric, hydroiodic, 2-hydroxyethanesulfonoic, hydroxymaleic, isethionic, lactic, maleic, malic, methanesulfonic, nicotinic, nitric, oxalic, palmic, pamoic, pectinic, persulfanilic, phenylacetic, phosphoric, pivalic, propionate, propionic, salicylic, stearic, succinic, sulfamic, sulfanilic, sulfuric, tartaric, thiocyanic, toluenesulfonic, tosylic, undecanoatehydrochloric, and the like. More preferred metallic salts include, but are not limited to appropriate alkali metal (group Ia) salts, alkaline earth metal (group IIa) salts and other physiological acceptable metals. Such salts can be made from aluminum, calcium, lithium, magnesium, potassium, sodium and zinc. Preferred organic salts can be made from tertiary amines and quaternary ammonium salts, including in part, tromethamine, diethylamine, N,N'-dibenzylethylenediamine, chloroprocaine, choline, diethanolamine, ethylenediamine, meglumine (N-methylglucamine) and procaine. All of these salts may be prepared by conventional means from the corresponding compound of Formulas I by reacting, for example, the appropriate acid or base with a compound of the present invention. The pharmaceutically acceptable salts of the present invention can be synthesized from the compounds of Formula I which contain a basic or acidic moiety by conventional chemical methods, for example, by reacting the free base or acid with stoichiometric amounts of the appropriate base or acid, respectively, in water or in an organic solvent, or in a mixture of the two (nonaqueous media like ether, ethyl acetate, ethanol, isopropanol, or acetonitrile are preferred) or by reacting the free base or acid with an excess of the desired salt-forming inorganic or organic acid or base in a suitable solvent or various combinations of solvents. Lists of suitable salts are found in Remington's Pharmaceutical Sciences, 17th ed., Mack Publishing Company, Easton, Pa., 1985, p. 1418, et al., the entire disclosure of which is incorporated herein by reference.

"Pharmaceutically effective" or "therapeutically effective" amount of a compound of the present invention is an amount that is sufficient to effect treatment, as defined herein, when administered to a mammal in need of such treatment. The amount will vary depending upon the subject and disease condition being treated, the weight and age of the subject, the severity of the disease condition, the manner of administration and the like, which can be readily determined by one of skill in the art.

"Regulate" or "Regulatory," as used herein means to control by enhancing, limiting, restricting, restraining, modulating or moderating. Such regulation includes the pleiotropic, redundant, synergistic or antagonistic effects that occur due to the activity of biological agents such as, without limitation, enzymes, cytokines, that can affect a variety of biological functions directly or indirectly through cascade or biofeedback mechanisms.

"Stable compound", as used herein, is a compound that is sufficiently robust to survive isolation to a useful degree of purity from a reaction mixture, and Formulation into an efficacious therapeutic agent, i.e., possesses stability that is sufficient to allow manufacture and that maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week. "Metabolically stable compound" denotes a compound that remains bioavailable when orally ingested by a mammal.

"Treatment" refers to any treatment of a COX-2 mediated disease or condition in a mammal, particularly a human, and includes, without limitation: (i) preventing the disease or condition from occurring in a subject which may be predisposed to the condition but has not yet been diagnosed with the condition and, accordingly, the treatment constitutes prophylactic treatment for the pathologic condition; (ii) inhibiting the disease or condition, i.e., arresting its development; (iii) relieving the disease or condition, i.e., causing regression of the disease or condition; or (iv) relieving the symptoms resulting from the disease or condition, e.g., relieving an inflammatory response without addressing the underlying disease or condition.

In view of the above non-limiting definitions, the present invention relates to a new class of compounds derived from suitable starting materials. In particular, the present invention provides sulfonyl-containing 2,3-diarylindole compounds, pharmaceutically acceptable derivatives (e.g., pharmaceutically acceptable racemic mixtures, resolved enantiomers, diastereomers, tautomers, salts and solvates thereof) or prodrugs thereof, having the following Formula I:

(I)

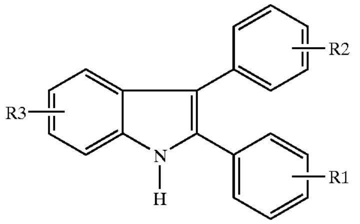

wherein each of $R_1$, $R_2$ and $R_3$ is independently selected from lower alkyl, lower haloalkyl, lower aralkyl, lower heterocyclicalkyl, lower heteroaralkyl, acyl, cyano, mercapto, lower alkoxy, lower alkylthio, lower alkylthioalkyl, lower alkylsulfonyl, lower haloalkylsulfonyl, lower arylsulfonyl, halo, lower hydroxyalkyl, lower alkoxyalkyl, lower alkenyloxyalkyl, lower alkylcarbonyl, lower arylcarbonyl, lower aralkylcarbonyl, lower cyanoalkyl, lower aralkenyl, lower aminoalkyl, lower alkylaminoalkyl, lower N-arylaminoalkyl, lower N-alkyl-N-arylaminoalkyl, lower carboxyalkyl, lower alkoxycarbonylalkyl, lower alkoxycarbonyl, lower haloalkylcarbonyl, carboxyl, aminocarbonyl, lower alkylaminocarbonyl, lower alkylaminocarbonylalkyl, lower aralkoxy, lower aralkylthio, phenylsulfonyl, lower aralkylsulfonyl, lower heteroaralkoxy, lower heteroaralkylthio, lower heteroarylalkoxyalkyl, lower heteroaryloxyalkyl, lower heteroarylthioalkyl, lower heteroarylalkylthioalkyl, heteroaryloxy, heteroarylthio, lower arylthioalkyl, lower aryloxyalkyl, lower arylthio, aryloxy, lower aralkylthioalkyl, lower aralkoxyalkyl, lower alkoxyaralkoxyalkyl, aryl and heteroaryl, wherein the aryl and heteroaryl radicals are optionally substituted at a substitutable position with one or more radicals selected from halo, lower alkylthio, lower alkylsulfinyl, lower alkyl, cyano, lower haloalkyl, lower hydroxyl, lower alkoxy, lower hydroxyalkyl and lower haloalkoxy. For instance, but without limitation, each of $R_1$, $R_2$ and $R_3$ may be a substituted or unsubstituted radical independently selected from the group consisting of: hydrido, fluoro, chloro, bromo, iodo, methyl, ethyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methylsulfonyl, aminosulfonyl, cyano, methoxy, ethoxy, isopropoxy, tert-butoxy, propoxy, butoxy, isobutoxy, pentoxy, methylenedioxy, amino, trifluoromethoxy, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, hydroxyl, nitro, methylsulfinyl, butylsulfinyl, hydroxymethyl, methoxymethyl, ethoxymethyl, methylamino, N,N-dimethylamino, phenylamino, methylthio, ethylthio, propylthio and butylthio.

In a more preferred embodiment, each of $R_1$ and $R_2$ is independently selected from the group consisting of 4-methylsulfonyl, 4-aminosulfonyl, hydrogen, 2-, 3-, or 4-halogen (example F, Cl or Br), $C_1$–$C_6$-alkyl, $C_1$–$C_4$-alkoxy, hydroxy, cyano, nitro, amino or trifluoromethyl; $R_3$ is hydrogen, 4-, 5-, 6-or 7- halogen, including F, Cl or Br, $C_1$–$C_6$-alkyl, $C_1$–$C_4$-alkoxy, hydroxy, cyano, nitro, amino or trifluoromethyl; with the proviso that $R_1$ is methylsulfonyl or aminosulfonyl, hydrogen, hydroxy, 4-halogen, including F, Cl or Br, 2-F, methoxy, 2-acetyloxy, 4-acetyloxy; $R_2$ is methylsulfonyl or aminosulfonyl, hydrogen, hydroxy, 4-halogen, including F, Cl or Br, 2-Cl, 3-Cl, methyl, 3,4-dimethyl, methoxy; $R_3$ is hydrogen, 5-halogen, including F, Cl or Br, 5-methyl;

Optionally, when $R_2$ is a methylsulfonyl or aminosulfonyl, $R_1$ is any one group as defined above.

In addition, the present invention also relates to pharmaceutical compositions comprising an effective amount of the compound of Formula I and a pharmaceutically acceptable carrier.

The present invention is also related to a method for treating inflammation or inflammatory disease in a subject in need of such treatment, the method comprises treating the subject with a therapeutically effective amount of a compound of the present invention.

On the one hand, the present invention is related to a method for preparing compounds of Formula I via a first Preparation Method A as set forth below.

There is a synthetic method in literature (Furstner, A.; Jumbam D. N. Tetrahedron. 1992, 48, 5991–6010) to prepare 2,3-diarylindole as a starting material. The method involves the preparation of substituted 2-amino-benzophenone from different starting material using Friedel-Crafts reaction, which was acylated in the presence of triethylamine to give the keto-amide compound, the cyclization of the amide by intramolecular condensation in the presence of $TiCl_4$ and Zn give rise to a compound of Formula (I). Specifically, the present method for preparing compounds of Formula I according to Preparation Method A comprises the following steps of:

- methylating p-methylthiophenol by dimethyl sulfate to give thioanisole;
- obtaining p-toluenesulfonamide by the reaction of toluenesulfonyl chloride with ammonia;
- oxidizing thioanisole (p-Toluenesulfonamide) by potassium permanganate to give rise to methylsulfonyl (aminosulfonyl) benzoic acid;
- refluxing substituted benzoic acid in thionyl chloride to give the corresponding benzoyl chloride;
- acylating anthranilic acid with p-toluenesulfonyl chloride give rise p-Toluenesulfonylanthranilic acid;
- preparing substituted 2-amino-benzophenone from different starting material using Friedel-Crafts reaction and hydrolysis, for example: p-Toluenesulfonylanthranilic acid with substituted benzene or substituted aniline with substituted benzoyl chloride;
- acylating the intermediate obtained above to give substituted 2-N-(substituted benzoyl)-amide-benzophenone; and
- cycling of the amide by intramolecular condensation in the presence of $TiCl_4$ and Zn give rise to the final compound.

Below is a chart illustrating the Preparation Method A:

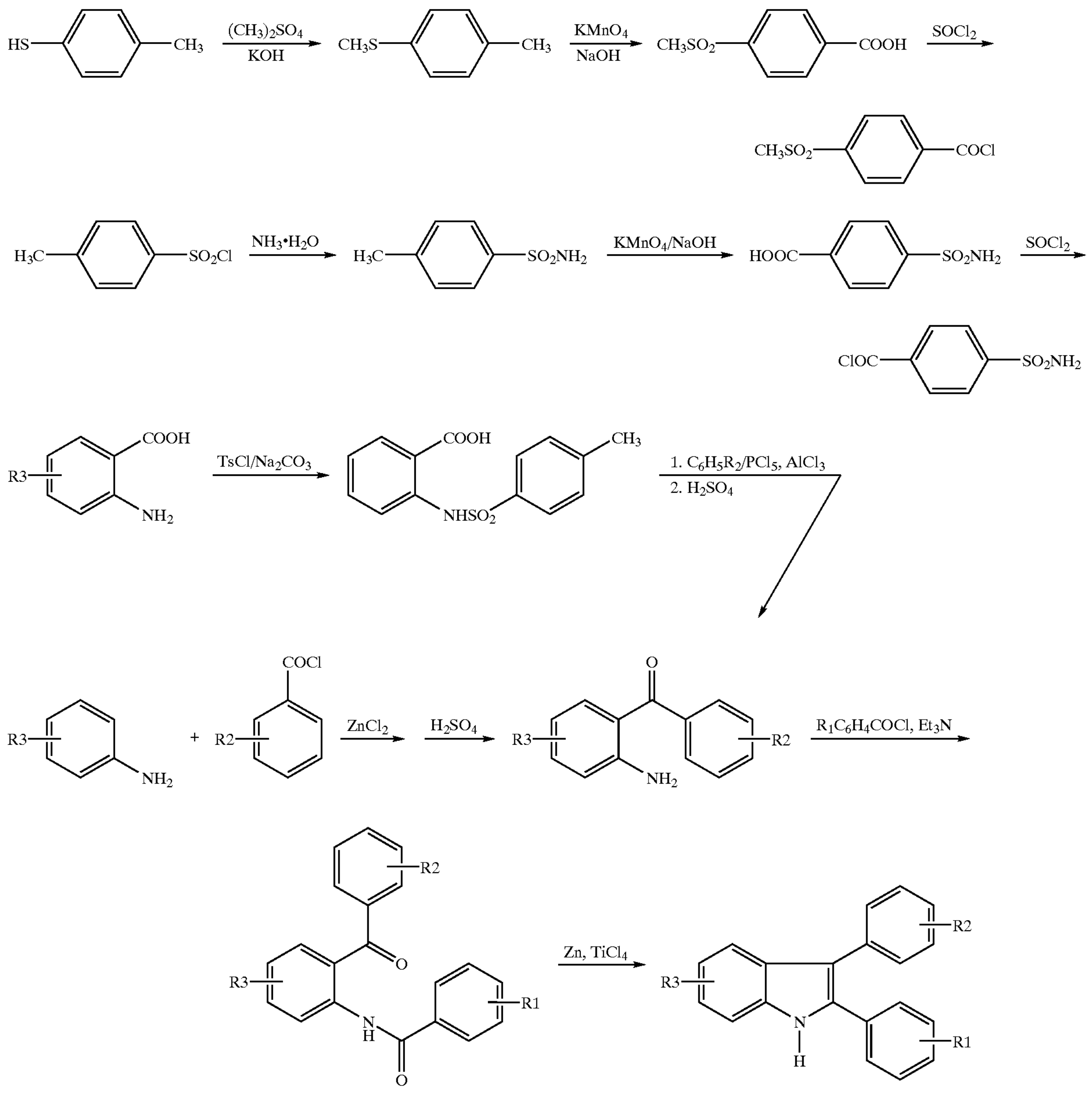

On the other hand, the present invention is also related to another method for preparing compounds of Formula I via a second Preparation Method B, as set forth below.

There is a synthetic method in literature (Robinson, B. The Fischer indole synthesis. Wiley, J. & Sons, New York, 1982.) to prepare 2,3-diarylindole. This method involves chloration of 4-methyl(amino)sulfonylphenylacetic acid using thionyl chloride and being taken Friedel-Crafts reaction to give rise to the corresponding substituted phenylacetophenone, which was condensed with substituted phenylhydrazine to give arylhydrazone, the arylhydrazone was finally cyclized to the target compound.

Specifically, the method for preparing compounds of Formula I according to Preparation Method B comprises the following steps of:

refluxing 4-methyl(amino)sulfonylphenylacetic acid in thionyl chloride to give the corresponding acyl chloride;

preparing substituted phenylacetophenone from the acyl chloride with substituted benzene by using Friedel-Crafts reaction;

converting condensation with substituted phenylhydrazine the substituted phenylacetophenone to arylhydrazone; and cycling the arylhydrazone to indole compound in the presence of a lewis acid.

Below is a chart illustrating the Preparation Method B:

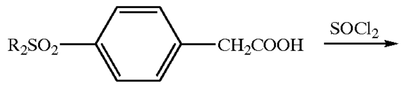

-continued

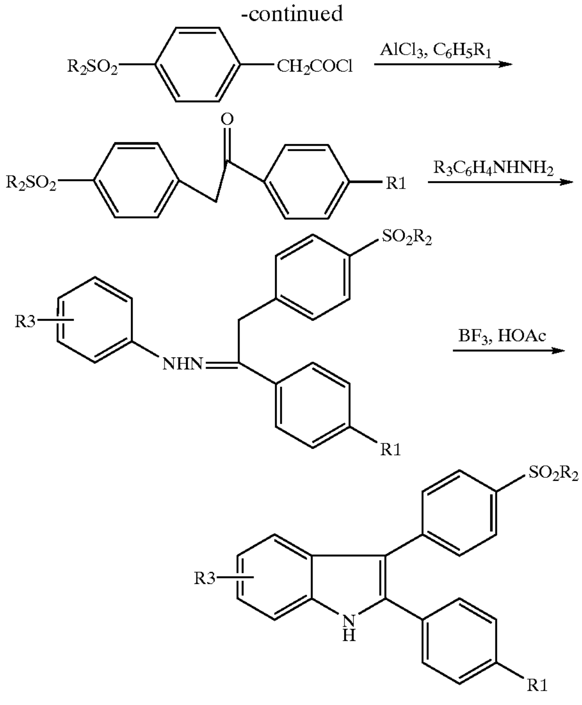

The present invention also provides pharmaceutical compositions which comprise a therapeutically effective amount of one or more of the compounds of Formula I.

In accordance with the principles of the present invention, the novel therapeutic compounds disclosed herein may contain one or more asymmetrically substituted carbon atoms and, thus, may occur as racemates and racemic mixtures, single enantiomers, diastereomeric mixtures and individual diastereomers. Each stereogenic carbon may be of the R or S configuration. Many geometric isomers of olefins, C—N double bonds, and the like can also be present in the compounds described herein, and all such stable isomers are contemplated in the present invention. It is well known in the art how to prepare optically active forms, such as by resolution of racemic forms or by synthesis from optically active starting materials. All chiral, diastereomeric, racemic forms and all geometric forms of a structure are intended to be encompassed within the present invention unless a specific stereochemistry or isomer form is specifically indicated. The stereoisomers of the compounds forming part of the present invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like or chiral bases such as rucine, cinchona alkaloids and their derivatives and the like.

Various polymorphs of the compound of general Formula I form part of the present invention and may be prepared by crystallization of the compound under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffractogram or such other techniques.

The compounds of the present invention may be modified by appending appropriate functionalites to enhance selective biological properties. Such modifications are known in the art and include, without limitation, those which increase penetration into a given biological compartment (e.g., blood, lymphatic system, central nervous system), increase oral or intravenous bioavailability, increase solubility to allow administration by injection, alter metabolism, alter rate of excretion, etc. The present invention also comprises the tautomeric forms of compounds of the present invention.

Compounds of Formula I possess inhibitory activity against COX-2, which is produced by the mediation of inflammatory substances. For instance, the compounds of Formula I significantly block mice ear edema induced by carrageenan. More importantly, the present invention preferably includes compounds which selectively inhibit COX-2 over COX-1. The inhibitory concentration of compounds of Formula I against COX-2 does not show any inhibition of COX-1, showing that the compounds are selective for the inhibition of COX-2 or for treatment of COX-2 mediated diseases, especially in the long-term clinical application the compounds of Formula I would exhibit less adverse reactions, such as less side effects for gastrointestinal and renal organs. It is preferred without limitation that the compounds of the present invention have a COX-2 $IC_{50}$ of less than about 0.5 $\mu$M, and also have a selectivity ratio of COX-2 inhibition over COX-1 inhibition of at least 5, and more preferably of at least 100. Even more preferably, the compounds have a COX-1 $IC_{50}$ of greater than about 2.5 $\mu$M, and more preferably of greater than 50 $\mu$M. Such preferred selectivity may indicate an ability to reduce the incidence of common NSAID-induced side effects.

The compound of Formula I is useful for relief of pain, fever, inflammation of a variety of conditions including rheumatic fever, symptoms associated with common cold, headache. In addition, COX-2 enzyme is highly expressed in colon and rectum carcinoma, such that a compound of the present invention would be useful for inhibiting cellular neoplastic transformations and hence can be used in the treatment of colon and rectum cancer.

The compounds of the present invention can be administered to a patient in such oral dosage forms as tablets, capsules, pills, or lozenges. Likewise, administration may be effected through parenteral route, such as injection or suppository. All these dosage forms are known to those of ordinary skilled in the arts. To manufacture of tablets, capsules or lozenges non-toxic pharmaceutically acceptable excipients may be for example inert diluents, such as starch, gelatin, acacia, silica, PEG; solvents for liquid dosage forms comprise water, ethanol, propylene glycol, vegetable oils such as corn oil, peanut oil and olive oil. Auxiliary in the dosage forms of the present invention comprises surface active agents, lubricates, disintegrators, sweeteners, disinfectants, and coloring agents.

The amount for active ingredient that may be combined with the carrier materials in a single dosage form will vary depending on the host treated and particular mode of administration. For example, a Formulation intended for the oral administration of patients may contain from 10 mg to 500 mg of a compound of Formula I. An optimal dosage form contains 20 mg to 100 mg of a compound of Formula I. By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of the present invention may be administered in a single daily dose, or the total daily dosage may be administered in divided doses of two, three, or four times daily.

An effective amount for treating can be easily and routinely determined by empirical methods known to those of skill in the art without undue experimentation utilizing the guidance provided hereunder coupled with knowledge that is known in the art, such as by establishing a matrix of dosages and frequencies of administration and comparing a group of experimental units or subjects to each point in the matrix. The exact amount to be administered to a patient will vary depending on the state and severity of the disorder and the physical condition of the patient. A measurable amelioration of any symptom or parameter can be determined by a physician skilled in the art or reported by the patient to the physician. It will be understood that any clinically or statistically significant attenuation or amelioration of any symptom or parameter of urinary tract disorders is within the scope of the invention. Clinically significant attenuation or amelioration means perceptible to the patient and/or to the physician or other practitioner. The specific dose level for any particular patient will depend upon a variety of factors including the age, body weight, general health, sex, diet, time of administration, route of administration, rate of excretion, drug combination, the severity of the particular disease undergoing therapy and the activity of the administered compound.

Compounds of the present invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues.

Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these-pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Representative useful pharmaceutical dosage-forms for administration of the compounds of the present invention can be illustrated as follows:

Capsules. A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules. A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets. Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable. A parenteral composition suitable for administration by injection may be prepared by stirring 1.5% by weight of active ingredient in 10% by volume propylene glycol and water. The solution should be made isotonic with sodium chloride and sterilized.

Suspension. An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of the present invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of the present invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are Formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the Formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

The compounds of the present invention may be administered in combination with one or more conventional agents, e.g., α-adrenergic antagonist, angiotensin II antagonist, angiotensin converting enzyme inhibitor, β-adrenergic antagonist, antiarrhythmic agent, antihypertensive, atriopeptidase inhibitor (alone or with ANP), β-blocker, calcium channel blocker, diuretic, digitalis, phosphodiesterase inhibitor, renin inhibitor, serotonin antagonist, sympatholytic agent and/or a vasodialoator. For example, acetazolamide, altizide, amiloride, aminophylline, amrinone, azosemide, atenolol, atriopeptin, bendroflumethiazide, benzapril, benzclortriazide, benzthiazide, butizide, candesartan, captopril, ceranopril, chlorothalidone, chlorothiazide, cilazapril, cilexetil, clonidine, cromakalim, cryptenamine acetates and cryptenamine tannates, cyclopenthiazide, cyclothiazide, delapril, deserpidine, diazoxide, digitalis, digoxin, diflusinal, diltiazem, dopamine, dobutamine, doxazosin, enalapril, enalaprilat, eprosartan, ethacrynic acid, ethiazide, felodipine, fosinopril, furosemide, guanabenz, guanethidine, guanethidine sulfate, hydralazine hydrochloride, hydrochlorothiazide, hydroflumethiazide, idrapril, imidapril, irbesartan, isradipine, ketanserin, libenzapril, lisinopril, losartan, merethoxylline procaine, methylchlothiazide, metolazone, metoprolol, metoprolol tartate, methyclothiazide, methyldopa, methyldopate hydrochloride, milrinone, minoxidil, moexipril, moveltopril, nadolol, nicardipine, nifedipine, niludipine, nimodipine, nisoldipine, nitrendipine, nitroglycerine, nitroprusside, pargyline hydrochloride, penflutazide, pentopril, perindopril, pinacidil, pindolol, polythiazide, prazosin, prentyl, propranolol, quinapril, quinapril hydrochloride, quinethazone, ramapril, rauwolfia serpentina, rescinnamine, reserpine, sodium ethacrynate, sodium nitroprusside, spirapril, spironolactone, synecor, tasosartan, telmisartan, temocapril, teprotide, terazosin, ticrynafan, timolol maleate, triamterene, trichlormethazide, trandolopril, trichlormethiazide, trimethophan camsylate, utibapril, valsartan, verapamil, zabicipril, zalicipril, zofenopril, zofenopril calcium, zolasartan, and the like, as well as admixtures and combinations thereof. Such compounds are known and normal daily dosages are well established. Typically, the individual daily dosages for these combinations may range from about one-fifth of the minimally recommended clinical dosages to the maximum recommended levels for the entities when they are given alone.

To illustrate these combinations, a COX-2 selective inhibitor compound of the present invention administered at a clinically effective dosage, is given within the daily dose range and is effectively combined, at levels which are equal or less than the daily dose range, with the following compounds at the indicated per day dose range: hydrochlorothiazide (6–200 mg), chlorothiazide (125–2000 mg), furosemide (5–80 mg), ethacrynic acid (5–200 mg), amiloride (5–20 mg), diltiazem (30–540 mg), felodipine(1–60 mg), nifedipine(5–120 mg), nitrendipine(5–60 mg), timolol maleate (1–60 mg), propanolol (10–480 mg), an angiotensin II antagonist, such as losartan (2.5–250 mg, preferably 50 mg), and methyldopa (65–2000 mg).

In addition, triple drug combinations of a COX-2 selective inhibitor compound of the present invention plus hydrochlorothiazide (15–200 mg), plus losartan (5–20 mg); or triple drug combinations of a COX-2 selective inhibitor compound of the present invention, plus hydrochlorothiazide (15–200 mg), plus amiloride (5–20 mg); or triple drug combinations of a COX-2 selective inhibitor, plus hydrochlorothiazide (15–200 mg), plus timolol maleate (5–60 mg); or triple drug combinations of COX-2 selective inhibitor, plus hydrochlorothiazide (15–200 mg), plus nifedipine (5–60 mg) are effective combinations to control blood pressure in hypertensive patients. Similarly, quadruple drug combinations of a COX-2 selective inhibitor compound of the present invention (1.0–200 mg), plus hydrochlorothiazide (15–200 mg), plus amiloride (5–20 mg), plus an angiotensin II antagonist (3–200 mg); or quadruple drug combinations of a COX-2 selective inhibitor compound of the present invention (1.0–200 mg), plus hydrochlorothiazide (15–200 mg), plus timolol maleate (5–60 mg), plus an angiotensin II antagonist (0.5–250 mg); or quadruple drug combinations of a COX-2 selective inhibitor compound of the present invention (1.0–200 mg), plus hydrochlorothiazide (15–200 mg), plus nifedipine (5–60 mg), plus an angiotensin II antagonist (0.5–250 mg) are also effective combinations to control blood pressure in hypertensive patients and/or provide benefit in the prevention or treatment of congestive heart failure. Naturally, these dose ranges may be adjusted on a unit basis as necessary to permit divided daily dosage and, as noted above, the dose will vary depending on the nature and severity of the disease, weight of patient, special diets and other factors.

To compare the inhibition of COX-1 and COX-2 by various compounds, numerous assays have been developed. The results from these assays are used to calculate a measure of COX-2 selectivity, and compounds are then compared to each other by ranking their COX-2 selectivity. The commonly used in vitro assays for assessing inhibition of COX-1 and COX-2 can be divided into two groups. The first consists of measuring the effect of inhibitors in assays of non-recombinant enzymes purified or partially purified from animal cells, or non-recombinant enzymes that are present in extracts or extract-fractions from animal cells or cell lines. These were the first tests to be developed and are historical in nature. The second type of assay uses human recombinant enzymes that have been expressed in human cell lines or human blood cells, typically platelets and monocytes. These are the current standard tests (Pairet et al., in Clinical Significance and Potential of Selective COX-2 Inhibitors, Vane, J. R. and Butting, R. M. (eds.), W. Harvey Press, pp.19–30, 1998).

The COX enzymes used in these assays can be of animal or human origin, they can be native or recombinant, and they can be used either as purified enzymes, microsomal preparations or whole cell assays. In addition, prostaglandin synthesis can be measured either from endogenously released arachidonic acid or from exogenously added arachidonic acid. In assays using recombinant COX-1 and COX-2 enzymes, the expression system used for gene replication and expression also varies. Not all assay systems require a COX-2 inducing agent. For instance, cells may be transfected with recombinant enzymes that are expressed constitutively. In other cell types, however, steps may be required to induce COX-2. In such cases, COX-2 is usually induced with either lipopolysaccharide (LPS) or cytokines, such as interleukin-1 (IL-1) or tumor necrosis factor (Pairet et al., in Clinical Significance and Potential of Selective COX-2 Inhibitors, Vane, J. R. and Butting, R. M. (eds.), W. Harvey Press, pp. 19–30, 1998).

In a preferred embodiment, measurement of inhibition of COX isozymes is performed in stably transfected Chinese hamster ovarian (CHO) cells expressing either human COX-1 or COX-2, as previously described (Riendeau et al., Br. J. Pharmacol. 121:105, 1997; Elrich et al., Clin. Pharm. Ther. 65: 336, 1999). Also preferred is where inhibition of COX isozymes is measured on constitutive and inducible forms of human cyclooxygenase (hCOX) cloned and expressed in insect cells (Spodoptera frugiperda), utilizing a baculovirus expression system. Expression of COX protein is determined by assessing PG-synthetic capability in homogenates from insect cells (Sf9 cells) incubated for 3 days with COX-1 or COX-2 recombinant baculovirus as previously described (Gierse et al., Biochem. J. 305: 479, 1995).

The inhibitory activity of a test compound can be measured for different isozymes, and the concentration inhibiting the enzyme activity by 50% ($IC_{50}$) can be calculated using regression analysis, or equivalent computational methods that are well-known in the art (Tallarida et al., Manual of Pharmacologic Calculations. Springer-Verlag, pp.10–12, 1981.)

As generally discussed above, compounds useful in practicing the present invention inhibit the COX-2 isozyme with an $IC_{50}$ of below 100 nM with at least about 10-fold, and preferably about 100-fold, higher potency for the COX-2 isozyme versus the COX-1 isozyme. It will be understood that measurements of inhibitory potency of a particular compound may vary depending upon the source of isozymes, as well as specific assay conditions.

To control for this type of variability, Compound A can be included in all assays as a standardization control. That is, the values of $IC_{50}$ obtained for compound A are compared to the values obtained with tested compounds for each assay. This allows a direct comparison of neurons absolute potency in inhibiting COX isozymes and ratios of inhibitory activities between different assays for the purpose of assessing whether the compound is within the scope of the invention.

A compound is considered to be a "selective" COX-2 inhibitor if it exhibits a selectivity ratio of at least 10-fold, i.e., the IC50 for COX-2 is at least 10-fold below the IC50 for COX-1. Once a compound is identified as possessing selectivity for the COX-2 isozyme, its pharmacological activity can be confirmed using one or more animal model systems for neuromuscular dysfunction of the lower urinary tract.

The following non-limiting examples further describe preferred compounds of the present invention and illustrate details for their preparation. Without being bound by the above general structural descriptions/definitions, preferred compounds of the present invention having usefulness as COX-2 inhibitors or regulating agents according to the present invention, include, but are not limited to, the compounds exemplified herein. Those skilled in the art will readily understand and appreciate that known variations of the conditions and procedures in the following preparative methods can be utilized. In these examples, all temperatures are in degrees Celsius, melting points are uncorrected. The Examples are illustrative only and do not limit the claimed invention regarding the materials, conditions, process parameters and the like recited herein.

EXAMPLES

Example 1 p-toluenesulfonamide 100 ml of ammonia (25%) was added in dropwise to toluenesulfonyl chloride (38.1 g, 0.2 mol) and stirred at room temperature for 4 h, refluxed for 10 min. After cooling, the solid was filtered off, washed with water, dried to give the title compound as white powder (31.2 g), yield 91.2%, m.p. 137–138° C.

Example 2

Thioanisole

To the solution of 17.6 g (0.14 mol) of p-methylthiophenol, 15.6 g (0.28 mol) of KOH in 100 ml of water cooled in the ice-water bath was added in dropwise 14.5 ml (0.15 mol) of dimethyl sulfate. After addition, the mixture was stirred for 5 h at room temperature, refluxed for 30 min, and then cooled, extracted with ether (3×100 ml), washed with aqueous sodium carbonate and water, dried over anhydrous $MgSO_4$. The solvent was removed and the residue was distilled in vacuo to give 14.6 g of the title compound as colorless oil at 104° C. (20 mmHg), yield 74.5%.

Preparation of p-amino(or Methyl)sulfonyl-benzoic acid

Example 3 p-aminosulfonyl-benzoic Acid

To the solution of 17.1 g (0.1 mol) of p-toluenesulfonamide prepared in Example 1, 20 g (0.5 mol) of sodium hydroxide in 300 ml of water was added in portions 20 g (0.13 mol) of potassium permanganate. The temperature raised to 70° C. spontaneously, keep the reaction mixture in 90° C. for 2 h. The mixture was then cooled and filtered, and the filtrate was acidified with HCl. The resulting precipitate was filtered, and washed with water, dried in vacuo to give the title compound (18.1 g) as white powder, yield 90%, m.p. 291–292° C.

Example 4 p-methylsulfonyl-benzoic Acid

The procedure was in the same manner as described in example 3, except that the starting material was 14.6 g (0.10 mol) of thioanisole prepared in Example 2 instead of 17.1 g (0.1 mol) of p-toluenesulfonamide. The title compound was obtained as white crystal, and yield 72.9%, m.p. 268–270° C.

Preparation of Substituted Benzoyl Chlorides

Example 6 p-sulfonamide-benzoyl Chloride

A mixture of 11.3 g (0.056 mol) of p-sulfonamidebenzoic acid prepared in Example 3 and 30 ml of thionyl chloride was heated under reflux to give a clear solution. Removal of the excess of thionyl chloride under reduced pressure obtained white solid and without purification put into the next reaction.

Example 5 p-methylsulfonyl-benzoyl Chloride

A mixture of 11.2 g (0.056 mol) of p-methylsulfonyl-benzoic acid prepared in Example 4 and 30 ml of thionyl chloride were heated under reflux to give a clear solution. Removal of the excess of thionyl chloride under reduced pressure obtained white solid and without purification put into the next reaction.

Example 7 p-Toluenesulfonylanthranilic Acid 13.7 g (0.1 mol) of anthranilic acid was added in three portions to the warmed solution of 26.0 g of sodium carbonate in 150 ml of water, 23.0 g (0.12 mol) of p-toluenesulfonyl chloride was added to the solution in 5 portions over a period of 20 minutes. Maintained the reaction mixture at 60–70° C. for additional 0.5 h, and rised to 85° C., 1.0 g of Norit was added cautiously and the solution was fitered. The filtrate was cooled and acidified with dilute HCl, the product was isolated by filtration and washed with dilute hydrochloric acid and then water. After recrystallized from 95% ethanol there was obtained the title compound (20.0 g) as white crystal, yield 68.7%, m.p. 229–232° C.

Preparation of Substituted 2-amino-benzophenone2

Example 8

2-amino-benzophenone

The mixture of 14.6 g (0.050 mol) of p-toluenesulfonylanthranilic acid prepared in Example 8 and 11.9 g (0.057 mol) of phosphorus pentachloride in 150 ml of dry benzene were heated at about 50° C. for 0.5 h. Cooled to 20–25° C. and 29.0 g (0.218 mol) of anhydrous aluminum chloride was added in portions. When addition was complete, the mixture was heated at 80–90° C. for 4 h and then cooled, poured onto a mixture of ice and 60 ml of 1N hydrochloride acid. The benzene was removed by vacuo distillation, the crude product was separated by filtration and washed with sodium carbonate and water. The filter cake is sucked reasonably dry, dissolved in 160 ml of conc. sulfuric acid and heated to 120° C. for 15 minutes. The reaction mixture was cooled and poured onto the mixture of ice and 1 g of norit, and the solution is filtered. The filtrate was neutralized with 12N ammonium hydroxide. The solid filtered off, washed with water and dried, recrystallized from 95% ethanol to give the title compound (6.63 g) as yellow crystal, yield 65.0%, m.p. 105–106° C.

Example 9

2-amino-4'-chloro-benzophenone

The procedure was in the same manner as described in example 8, except that the starting material was chlorobenzene instead of benzene. The title compound was obtained as golden yellow needle crystal, and yield 57.9%, m.p. 100.5–101.5° C.

Example 10

2-amino-4'-bromo-benzophenone

The procedure was in the same manner as described in example 8, except that the starting material was bromobenzene instead of benzene. The title compound was obtained as golden yellow crystal, and yield 49.7%, m.p. 104–106° C.

Example 11

2-amino-4'-methyl-benzophenone

The procedure was in the same manner as described in example 8, except that the starting material was toluene instead of benzene. The title compound was obtained as yellow crystal, and yield 67.2%, m.p. 89–91° C.

Example 12

2-amino-3,4'-dimethyl-benzophenone

The procedure was in the same manner as described in example 8, except that the starting material was 3,4'-dimethylbenzene instead of benzene. The title compound was obtained as yellow solid, and yield 35.5%, m.p. 77–78° C.

Example 13

2-amino-4'-methoxy-benzophenone

The procedure was in the same manner as described in example 8, except that the starting material was anisole instead of benzene. The title compound was obtained as yellow crystal, and yield 57.3%, m.p. 76–77° C.

Example 14

2-amino-4'-fluoro-benzophenone

The procedure was in the same manner as described in example 8, except that the starting material was fluorobenzene instead of benzene. The title compound was obtained as yellow solid, m.p. 124–125° C., and yield 53.7%.

Example 15

2-amino-5-chloro-4'-chloro-benzophenone

A mixture of 21.0 g (0.135 mol) of p-chlorobenzoic acid and 20 ml of thionyl chloride were heated under reflux to give a clear solution. Removal of the excess of thionyl chloride under reduced pressure obtained white solid and immediately used for the next reaction. To the benzoyl chloride heated to 120° C. was added in portions with stirring 6.3 g (0.05 mol) of 4-chloroaniline. The mixture was heated to 180° C. and 8.5 g (0.063 mol) of ZnCl2 was added. The temperature was gradually increased to about 205° C. and kept there for 2 h. After cooling to 120° C., 60 ml of 3NHCl was added and the mixture stirred and heated to reflux. The hot acid layer was decanted and this procedure repeated two or three times. The water-insoluble residue was dissolved in 80 ml of 70% sulfuric acid and reflux for 8 h and then, after cooling poured into a large amount of ice water. The reaction mixture was neutralized with aqueous ammonia hydroxy and extracted with ethyl acetate, dried over Na2SO4. The solvent was removed and the residue was crystallized from 95% ethanol to give the title compound as golden yellow crystal 5.1 g, and yield 38.5%, m.p. 106–107° C.

Example 16

2-amino-5-chloro-benzophenone

The procedure was in the same manner as described in example 15, except that the starting material was benzoic acid instead of p-chlorobenzoic acid. The title compound was obtained as yellow needle crystal, and yield 44.9%, m.p. 97–98° C.

Example 17

2-amino-5-chloro-2'-chloro-benzophenone

The procedure was in the same manner as described in example 15, except that the starting material was o-chlorobenzoic acid instead of p-chlorobenzoic acid. The title compound was obtained as yellow needle crystal, and yield 44.2%, m.p. 94–95° C.

Example 18

2-amino-5-fluoro-benzophenone

The procedure was in the same manner as described in example 15, except that the starting material was benzoic acid instead of p-chlorobenzoic acid and 4-fluoroaniline instead of 4-chloroaniline. The title compound was obtained as yellow needle crystal, and yield 37.9%, m.p. 112–113° C.

Example 19

2-amino-5-bromo-benzophenone

The procedure was in the same manner as described in example 15, except that the starting material was benzoic acid instead of p-chlorobenzoic acid and 4-bromoaniline instead of 4-chloroaniline. The title compound was obtained as yellow needle crystal, and yield 19.8%, m.p.109–110° C.

Example 20

2-amino-5-methyl-benzophenone

The procedure was in the same manner as described in example 15, except that the starting material was benzoic acid instead of p-chlorobenzoic acid and p-toluidine instead of 4-chloroaniline. The title compound was obtained as yellow needle crystal, and yield 49.3%, m.p. 64–66° C.

Example 21

2-amino-5-chloro-3'-chloro-benzophenone

The procedure was in the same manner as described in example 15, except that the starting material was m-chlorobenzoic acid instead of p-chlorobenzoic acid. The title compound was obtained as golden yellow crystal, and yield 13.4%, m.p. 118–119° C.

Example 22

2-amino-5-chloro-4'-methylsulfonyl-benzophenone

The procedure was in the same manner as described in example 15, except that the starting material was p-methylsulfonyl-benzoic acid instead of p-chlorobenzoic acid. The title compound was obtained as yellow needle crystal, m.p.176–177° C., and yield 40.9%.

Preparation of Substituted 2-N-(Substituted Benzoyl)-amide-benzophenones

Example 23

2-N-(4-methylsulfonylbenzoyl)-amide-benzophenone

To a solution of 2.0 g (0.010 mol) of 2-amino-benzophenone prepared in Example 8, 1.6 ml (0.011 mol) of triethylamine in 20 ml of dry THF under nitrogen was added a solution of 2.0 g (0.010 mol) of 4-methylsulfonylbenzoyl chloride in 10 ml of dry THF. The reaction mixture was stirred at room temperature for 2 h, and filtered. The filtrate was concentrated and the residue was purified by column chromatograph on silica gel (eluent: petroleum eter: ethyl acetate, 3:1) to give the title compound as white needle crystal, yield 68.2%, m.p. 177–178° C.

Example 24

2-N-(4-aminosulfonylbenzoyl)-amide-benzophenone

To a solution of 2.0 g (0.010 mol) of 2-amino-benzophenone prepared in Example 8, 1.6 ml (0.011 mol) of triethylamine in 20 ml of dry THF under nitrogen was added a solution of 2.0 g (0.010 mol) of 4-aminosulfonylbenzoyl chloride in 10 ml of dry THF. The reaction mixture was stirred at room temperature for 2 h, and filtered. The filtrate was concentrated and the residue was purified by column chromatograph on silica gel (eluent: petroleum ester: ethyl acetate, 1:1) to give the title compound as white needle crystal, yield 59.5%, m.p. 216–218° C.

Example 25

2-N-(4-methylsulfonylbenzoyl)-amide-4'-chloro-benzophenone

The procedure was in the same manner as described in example 23, except that the starting material was 2-amino-4'-chloro-benzophenone prepared in Example 9 instead of 2-amino-benzophenone. The title compound was obtained as white solid, and yield 75.7%, m.p. 186–188° C.

Example 26

2-N-(4-aminosulfonylbenzoyl)-amide-4'-chloro-benzophenone

The procedure was in the same manner as described in example 24, except that the starting material was 2-amino-4'-chloro-benzophenone prepared in Example 9 instead of 2-amino-benzophenone. The title compound was obtained as light yellow solid, and yield 53.6%, m.p. 198–200° C.

Example 27

2-N-(4-methylsulfonylbenzoyl)-amide-4'-bromo-benzophenone

The procedure was in the same manner as described in example 23, except that the starting material was 2-amino-4'-bromo-benzophenone prepared in example 10 instead of 2-amino-benzophenone. The title compound was obtained as white solid, and yield 67.5%, m.p.176–178° C.

Example 28

2-N-(4-aminosulfonylbenzoyl)-amide-4'-bromo-benzophenone

The procedure is in the same manner as described in example 24, the starting material was 2-amino-4'-bromo-benzophenone prepared in example 10 instead of 2-amino-benzophenone. The title compound obtained was directly put into next reaction without purification.

Example 29

2-N-(4-methylsulfonylbenzoyl)-amide-4'-methyl-benzophenone

The procedure was in the same manner as described in example 23, except that the starting material was 2-amino-4'-methyl-benzophenone prepared in Example 11 instead of 2-amino-benzophenone. The title compound was obtained as light yellow crystal, yield 77.9%, and m.p. 171–173° C.

Example 30

2-N-(4-aminosulfonylbenzoyl)-amide-4'-methyl-benzophenone

The procedure was in the same manner as described in example 24, except that the starting material was 2-amino-4'-methyl-benzophenone prepared in Example 11 instead of 2-amino-benzophenone. The title compound was obtained as white solid, and yield 12.0%, m.p. 216–218° C.

Example 31

2-N-(4-methylsulfonylbenzoyl)-amide-3',4'-dimethyl-benzophenone

The procedure was in the same manner as described in example 23, except that the starting material was 2-amino-3',4'-dimethyl-benzophenone prepared in Example 12 instead of 2-amino-benzophenone. The title compound was obtained as light yellow solid, yield 41.3%, and m.p. 206–207° C.

Example 32

2-N-(4-aminosulfonylbenzoyl)-amide-3',4'-dimethyl-benzophenone

The procedure was in the same manner as described in example 24, except that the starting material was 2-amino-3',4'-dimethyl-benzophenone prepared in Example 12 instead of 2-amino-benzophenone. The title compound was obtained as light yellow solid, yield 49.6%, and m.p. 251–253° C.

Example 33

2-N-(4-methylsulfonylbenzoyl)-amide-4'-methoxy-benzophenone

The procedure was in the same manner as described in example 23, except that the starting material was 2-amino-4'-methoxy-benzophenone prepared in Example 13 instead of 2-amino-benzophenone. The title compound was obtained as light yellow crystal, yield 32.4%, and m.p. 160–161° C.

Example 34

2-N-(4-aminosulfonylbenzoyl)-amide-4'-methoxy-benzophenone

The procedure was in the same manner as described in example 24, except that the starting material was 2-amino-4'-methoxy-benzophenone prepared in Example 13 instead of 2-amino-benzophenone. The title compound was obtained as light yellow crystal, yield 55.3%, and m.p. 173–174° C.

Example 35

2-N-(4-methylsulfonylbenzoyl)-amide-4'-fluoro-benzophenone

The procedure was in the same manner as described in example 23, except that the starting material was 2-amino-4'-fluoro-benzophenone prepared in Example 14 instead of 2-amino-benzophenone. The title compound was obtained as light yellow crystal, yield 76.7%, and m.p. 175–177° C.

Example 36

2-N-(4-aminosulfonylbenzoyl)-amide-4'-fluoro-benzophenone

The procedure was in the same manner as described in example 24, except that the starting material was 2-amino-4'-fluoro-benzophenone prepared in Example 14 instead of 2-amino-benzophenone. The title compound was obtained as light yellow crystal, yield 44.8%,and m.p. 204–206° C.

Example 37

2-N-(4-methylsulfonylbenzoyl)-amide-5-chloro-4'-chloro-benzophenone

The procedure was in the same manner as described in example 23, except that the starting material was 2-amino- 5-chloro-4'-chloro-benzophenone prepared in Example 15 instead of 2-amino-benzophenone. The title compound was obtained a white solid, yield 93.0%, and m.p. 211–213° C.

Example 38

2-N-(4-aminosulfonylbenzoyl)-amide-5-chloro-4'-chloro-benzophenone

The procedure was in the same manner as described in example 24, except that the starting material was 2-amino-5-chloro-4'-chloro-benzophenone prepared in Example 15 instead of 2-amino-benzophenone. The title compound was obtained as needle yellow crystal, yield 76.2%, and m.p. 234–236° C.

Example 39

2-N-(4-aminosulfonylbenzoyl)-amide-5'-chloro-benzophenone

The procedure was in the same manner as described in example 24, except that the starting material was 2-amino-5'-chloro-benzophenone prepared in Example 16 instead of 2-amino-benzophenone. The title compound was obtained as white solid, yield 28.9%, and m.p. 231–233° C.

Example 40

2-N-(4-methylsulfonylbenzoyl)-amide-5'-chloro-benzophenone

The procedure was in the same manner as described in example 23, except that the starting material was 2-amino-5'-chloro-benzophenone prepared in Example 16 instead of 2-amino-benzophenone. The title compound was obtained as white solid, yield 50.7%, and m.p. 184–185° C.

Example 41

2-N-(4-aminosulfonylbenzoyl)-amino-5-chloro-2'-chloro-benzophenon

The procedure was in the same manner as described in example 24, except that the starting material was 2-amino-5-chloro-2'-chloro-benzophenone prepared in Example 17 instead of 2-amino-benzophenone. The title compound was obtained as light yellow solid, yield 48.3%, and m.p. 219–221° C.

Example 42

2-N-(4-methylsulfonylbenzoyl)-amino-5-chloro-2'-chloro-benzophenone

The procedure was in the same manner as described in example 23, except that the starting material was 2-amino-5-chloro-2'-chloro-benzophenone prepared in Example 17 instead of 2-amino-benzophenone. The title compound was obtained as white solid, yield 80.1%, and m.p. 231–233° C.

Example 43

2-N-(4-methylsulfonylbenzoyl)-amide-5-fuoro-benzophenone

The procedure was in the same manner as described in example 23, except that the starting material was 2-amino-5-fluoro-benzophenone prepared in Example 18 instead of 2-amino-benzophenone. The title compound was obtained as white crystal, yield 76.7%, and m.p. 175–177° C.

Example 44

2-N-(4-aminosulfonylbenzoyl)-amide-5-fuoro-benzophenone

The procedure was in the same manner as described in example 24, except that the starting material was 2-amino-5-fluoro-benzophenone prepared in Example 18 instead of 2-amino-benzophenone. The title compound was obtained as white solid, yield 49.9%, and m.p. 204–206° C.

Example 45

2-N-(4-aminosulfonylbenzoyl)-amide-5-bromo-benzophenone

The procedure was in the same manner as described in example 24, except that the starting material was 2-amino-5-bromo-benzophenone prepared in Example 19 instead of 2-amino-benzophenone. The title compound was obtained as light yellow solid, yield 40.2%, and m.p. 234–236° C.

Example 46

2-N-(4-methylsulfonylbenzoyl)-amide-5-bromo-benzophenone

The procedure was in the same manner as described in example 23, except that the starting material was 2-amino-5-bromo-benzophenone prepared in Example 19 instead of 2-amino-benzophenone. The title compound was obtained as white solid, yield 41.85%, and m.p. 185.5–186.5° C.

Example 47

2-N-(4-methylsulfonylbenzoyl)-amide-5-methyl-benzophenone

The procedure was in the same manner as described in example 23, except that the starting material was 2-amino-5-methyl-benzophenone prepared in Example 20 instead of 2-amino-benzophenone. The title compound was obtained a white crystal, yield 85.0%, m.p. 174–176° C.

Example 48

2-N-(4-aminosulfonylbenzoyl)-amide-5-methyl-benzophenone

The procedure was in the same manner as described in example 24, except that the starting material was 2-amino-5-methyl-benzophenone prepared in Example 20 instead of 2-amino-benzophenone. The title compound was obtained as light yellow solid, yield 60.3%, m.p. 247–249° C.

Example 49

2-N-(4-aminosulfonylbenzoyl)-amide-5-chloro-3'-chloro-benzophenone

The procedure was in the same manner as described in example 24, except that the starting material was 2-amino-5-chloro-3'-chloro-benzophenone prepared in Example 21 instead of 2-amino-benzophenone. The title compound was obtained as white needle crystal, yield 63.5%, m.p. 215–217° C.

Example 50

2-N-(4-methylsulfonylbenzoyl)-amide-5-chloro-3'-chloro-benzophenone

The procedure was in the same manner as described in example 23, except that the starting material was 2-amino- 5-chloro-3'-chloro-benzophenone prepared in Example 21 instead of 2-amino-benzophenone. The title compound was obtained as white needle crystal, yield 71.2%, m.p. 147–148° C.

Example 51

2-N-(benzoyl)-amide-5-chloro-4'-methylsulfonyl-benzophenone

To a solution of 3.1 g (0.010 mol) of 2-amino-4'-methylsulfonyl-benzophenone prepared in Example 22, 1.6 ml (0.011 mol) of triethylamine in 20 ml of dry THF under nitrogen was added a solution of 1.4 g (0.010 mol) of benzoyl chloride in 10 ml of dry THF. The reaction mixture was stirred at room temperature for 2 h, and filtered. The filtrate was concentrated and the residue was purified by column chromatograph on silica gel (eluent: petroleum eter: ethyl acetate, 3:1) to give the title compound as light yellow needle crystal, yield 74.8%, m.p. 203–205° C.

Example 52

2-N-(4-methylsulfonylbenzoyl)-amide-5-chloro-4'-methylsulfonylbenzophenone

The procedure was in the same manner as described in example 51, except that the starting material was 4-methylsulfonyl-benzoyl chloride instead of benzoyl chloride. The title compound was obtained as light yellow solid, yield 46.8%, m.p. 173–175° C.

Example 53

2-N-(4-chlorobenzoyl)-amide-5-chloro-4'-methylsulfonyl-benzophenone

The procedure was in the same manner as described in example 51, except that the starting material was 4-chlorobenzoyl chloride instead of benzoyl chloride. The title compound was obtained as light yellow crystal, yield 81.5%, m.p. 196–196° C.

Example 54

2-N-(4-methoxybenzoyl)-amide-5-chloro-4'-methylsulfonyl-benzophenone

The procedure was in the same manner as described in example 51, except that the starting material was 4-methoxybenzoyl chloride instead of benzoyl chloride. The title compound was obtained as green yellow crystal, yield 48.9%, m.p. 163–165° C.

Example 55

2-N-(4-methylbenzoyl)-amide-5-chloro-4'-methylsulfonyl-benzophenone

The procedure was in the same manner as described in example 51, except that the starting material was 4-methylbenzoyl chloride instead of benzoyl chloride. The title compound was obtained as light yellow crystal, yield 62.1%, m.p. 178–180° C.

Example 56

2-N-(2-fluorobenzoyl)-amide-5-chloro-4'-methylsulfonyl-benzophenone

The procedure was in the same manner as described in example 51, except that the starting material is fluorobenzoyl choride instead of benzoyl chloride. The title compound was obtained as light yellow solid, yield 61.5%, m.p. 171–173° C.

Example 57

2-N-(2-acetyloxylbenzoyl)-amide-5-chloro-4'-methylsulfonyl-benzophenone

The procedure was in the same manner as described in example 51, except that the starting material was 2-acetyloxybenzoyl choride instead of benzoyl chloride. The title compound was obtained as light yellow solid, yield 65.6%, m.p. 206–208° C.

Example 58

2-N-(4-acetyloxylbenzoyl)-amide-5-chloro-4'-methylsulfonyl-benzophenone

The procedure was in the same manner as described in example 51, except that the starting material was 4-acetyloxybenzoyl choride instead of benzoyl chloride. The title compound was obtained as white crystal, yield 67.0%, m.p. 238–240° C.

Preparation of 2-[4-methyl(amino)sulfonylphenyl]-3-sustituted-phenylindoles

Example 59

2-(4-methylsulfonylphenyl)-3-phenylindole 1.14 g (3 m mol) of 2-N-(4-methylsulfonylbenzoyl)-amide-benzophenone prepared in Example 23, 0.87 g (12 m mol) of 90% Zn was suspended in 20 ml dry THF. To the mixture 0.7 ml (6.2 m mol) of $TiCl_4$ was added dropwise and heated to reflux for 1.5 h. The solvent was removed in vacuo and the residue was purified by column chromatography using petroleum ether/ ethyl acetate (3/1) as elutant. The title compound (0.45 g) was obtained as white crystal, yield 56.2%, m.p. 221–222° C. Analysis via Nuclear Magnetic Resonance provided the following information: $^1$HNMR (DMSO)δ: 3.23 (s, 3H, $SO_2CH_3$), 7.03–7.49 (m, 9H, Ar—H), 7.55–8.15 (dd, 4H, Ar—H), 11.67 (s, 1H, N—H); Anal. Calcd for: $C_{21}H_{17}NO_2S$: C 72.60, H 4.93, N 4.03; Found: C 72.39, H 5.14, N 3.83.

Example 60

2-(4-aminosulfonylphenyl)-3-phenylindole

The procedure was in the same manner as described in example 59, except that the starting material is 2-N-(4-aminosulfonylbenzoyl)-amide-benzophenone prepared in Example 24 instead of 2-N-(4-methylsulfonylbenzoyl)-amide-benzophenone. The title compound was obtained as white crystal, yield 43.9%, m.p. 231–232° C. The data of Nuclear Magnetic Resonance shown that: $^1$HNMR (300 MHz, DMSO)δ: 7.03–7.49 (m, 9H, Ar—H), 7.65–7.89 (dd, 4H, Ar—H), 10.8 (s, 1H, N—H); Anal. Calcd for: $C_{20}H_{16}N_2O_2S$: C 68.94, H 4.63, N 8.04; Found: C 68.99, H 4.61, N 8.18.

Example 61

2-(4-methylsulfonylphenyl)-3-(4-chlorophenyl) indole

The procedure was in the same manner as described in example 59, except that the starting material was 2-N-(4- methylsulfonylbenzoyl)-amide-4'-chloro-benzophenone prepared in Example 25 instead of 2-N-(4-methylsulfonylbenzoyl)-amide-benzophenone. The title compound was obtained as white crystal, yield 65.5%, m.p. 198.5–200.5° C. The data of Nuclear Magnetic Resonance shown that: $^1$HNMR (300 MHz, $CDCl_3$)δ:3.09 (s, 3H, $SO_2CH_3$), 7.16–7.85 (m, 12H, Ar—H), 8.65 (s,1H, N—H ); Anal. Calcd for: $C_{21}H_{16}ClNO_2S$: C 66.05, H 4.22, N 3.67; Found: C 66.03, H 4.48, N 3.64.

Example 62

2-(4-aminosulfonylphenyl)-3-(4-chlorophenyl)indole

The procedure was in the same manner as described in example 59, except that the starting material is 2-N-(4-aminosulfonylbenzoyl)-amide-4'-chloro-benzophenone prepared in Example 26 instead of 2-N-(4-methylsulfonylbenzoyl)-amide-benzophenone. The title compound was obtained as white crystal, yield 73.9%, m.p. 298–300° C. Analysis via Nuclear Magnetic Resonance provided the following information: $^1$HNMR (300 MHz, DMSO)δ: 3.29 (s, 2H, $SO_2NH_2$), 7.05–7.50 (m, 8H, Ar—H), 7.53–7.81(dd, 4H, Ar—H), 11.75 (s, 1H, N—H); Anal. Calcd for: $C_{20}H_{15}ClN_2O_2S$: C 62.74, H 3.95, N 7.35; Found: C 62.68, H 3.77, N 7.44.

Example 63

2-(4-methylsulfonylphenyl)-3-(4-bromophenyl) indole

The procedure was in the same manner as described in example 59, except that the starting material was 2-N-(4-methylsulfonylbenzoyl)-amide-4'-bromo-benzophenone prepared in Example 27 instead of 2-N-(4-methylsulfonylbenzoyl)-amide-benzophenone. The title compound was obtained as white crystal, yield 75.2%, m.p. 225–226° C. Analysis via Nuclear Magnetic Resonance provided the following information: 1HNMR (300 MHz, DMSO)δ:3.09 (s, 3H, $SO_2CH_3$), 7.16–7.84 (m, 12H, Ar—H), 8.69 (s, 1H, N—H ); Anal. Calcd for: C21H16BrNO2S: C 59.16, H 3.78, N 3.29; Found: C 59.04, H 3.85, N 3.20.

Example 64

2-(4-aminosulfonylphenyl)-3-(4-bromophenyl)indole

The procedure was in the same manner as described in example 59, except that the starting material was 2-N-(4-aminosulfonylbenzoyl)-amide-4'-bromo-benzophenone prepared in Example 28 instead of 2-N-(4-methylsulfonylbenzoyl)-amide-benzophenone. The title compound was obtained as white crystal, yield 11.7%, m.p. 277–279° C. Analysis via Nuclear Magnetic Resonance provided the following information: $^1$HNMR (300 MHz, $CDCl_3$)δ:3.23 (s, 2H, $SO_2NH_2$), 7.04–7.80 (m, 12H, Ar—H), 11.70 (s, 1H, N—H); Anal. Calcd for: $C_{20}H_{15}BrNO_2S$: C 56.21, H 3.54, N 6.56; Found: C 56.46, H 3.70, N 6.72.

Example 65

2-(4-methylsulfonylphenyl)-3-(4-methylphenyl) indole

The procedure was in the same manner as described in example 59, except that the starting material is 2-N-(4-methylsulfonylbenzoyl)-amide-4'-methyl-benzophenone prepared in Example 29 instead of 2-N-(4-methylsulfonylbenzoyl)-amide-benzophenone. The title compound was obtained as white crystal, yield 77.4%, m.p. 197–198° C. Analysis via Nuclear Magnetic Resonance provided the following information: $^1$HNMR (300 MHz, DMSO)δ: 2.35 (s, 3H, $CH_3$), 3.21 (s, 3H, $SO_2CH_3$), 7.01–7.88 (m, 12H, Ar—H), 11.64 (s, 1H, N—H); Anal. Calcd for: $C_{22}H_{19}NO_2S$: C 73.10, H 5.02, N 3.88; Found: C 72.82, H 5.42, N 3.97.

Example 66

2-(4-aminosulfonylphenyl)-3-(4-methylphenyl) indole

The procedure was in the same manner as described in example 59, except that the starting material was 2-N-(4-aminosulfonylbenzoyl)-amide-4'-methyl-benzophenone prepared in Example 30 instead of 2-N-(4-methylsulfonylbenzoyl)-amide-benzophenone. The title compound was obtained as white crystal, yield 55.3%, m.p. 293–295° C. Analysis via Nuclear Magnetic Resonance provided the following information: $^1$HNMR (300 MHz, DMSO)δ:2.34 (s, 3H, $CH_3$), 3.43 (s, 2H, $SO_2NH_2$), 7.01–7.77 (m, 12H, Ar—H), 11.59 (s, 1H, N—H); Anal. Calcd for: $C_{21}H_{18}N_2O_2S$: C 69.60, H 5.01, N 7.73; Found: C 69.45, H 5.25, N 7.53.

Example 67

2-(4-methylsulfonylphenyl)-3-(3,4-dimethylphenyl) indole

The procedure was in the same manner as described in example 59, except that the starting material was 2-N-(4-methylsulfonylbenzoyl)-amide-3',4'-dimethyl-benzophenone prepared in Example 31 instead of 2-N-(4-methylsulfonylbenzoyl)-amide-benzophenone. The title compound was obtained as white crystal, yield 67.0%, m.p. 206–207° C. The data of Nuclear Magnetic Resonance shown that: $^1$HNMR (300 MHz, DMSO)δ:2.23 (s, 3H, $CH_3$), 2.26 (s, 3H, $CH_3$), 3.21 (s, 3H, $SO_2CH_3$), 6.99–7.88 (m, 11H, Ar—H), 11.62 (s, 1H, N—H); Anal. Calcd for: $C_{23}H_{21}NO_2S$: C 73.57, H 5.64, N 3.73; Found: C 73.32, H 5.65, N 3.58.

Example 68

2-(4-aminosulfonylphenyl)-3-(3,4-dimethylphenyl) indole

The procedure was in the same manner as described in example 59, except that the starting material was 2-N-(4-aminosulfonylbenzoyl)-amide-3',4'-dimethyl-benzophenone prepared in Example 32 instead of 2-N-(4-methylsulfonylbenzoyl)-amide-benzophenone. The title compound was obtained as white crystal, yield 49.6%, m.p. 251–253° C. Analysis via Nuclear Magnetic Resonance provided the following information: $^1$HNMR (300 MHz, DMSO)δ:2.24 (s, 3H, $CH_3$), 2.26 (s, 3H, $CH_3$), 3.43 (s, 2H, $SO_2NH_2$), 7.00–7.78 (m, 1H, Ar—H), 11.64 (s, 1H, N—H); Anal. Calcd for: $C_{22}H_{20}N_2O_2S$: C 70.19, H 5.35, N 7.44; Found: C 70.13, H 5.42, N 7.33.

Example 69

2-(4-methylsulfonylphenyl)-3-(4-methoxyphenyl) indole

The procedure was in the same manner as described in example 59, except that the starting material was 2-N-(4- methylsulfonylbenzoyl)-amide-4'-methoxy-benzophenone prepared in Example 33 instead of 2-N-(4-methylsulfonylbenzoyl)-amide-benzophenone. The title compound was obtained as white crystal, yield 74.7%, m.p. 218.5–220.5° C. The data of Nuclear Magnetic Resonance shown that: $^1$HNMR (300 MHz, $CDCl_3$)δ:3.08 (s, 3H, $SO_2CH_3$), 3.87 (s, 3H, $OCH_3$),6.95–7.86 (m, 12H, Ar—H), 8.41 (s,1H, N—H); Anal. Calcd for: $C_{22}H_{19}NO_3S$: C 69.98, H 5.07, N 3.71; Found: C 69.90, H 5.12, N 3.99.

Example 70

2-(4-aminosulfonylphenyl)-3-(4-methoxyphenyl) indole

The procedure was in the same manner as described in example 59, except that the starting material was 2-N-(4-aminosulfonylbenzoyl)-amide-4'-methoxy-benzophenone prepared in Example 34 instead of 2-N-(4-methylsulfonylbenzoyl)-amide-benzophenone. The title compound was obtained as white crystal, yield 73.9%, m.p. 280–282° C. Analysis via Nuclear Magnetic Resonance provided the following information: $^1$HNMR (300 MHz, DMSO)δ:3.28 (s, 2H, $SO_2NH_2$), 3.79 (s, 3H, $OCH_3$), 6.97–7.78 (m, 12H, Ar—H), 11.59 (s, 1H, N—H); Anal. Calcd for: $C_{21}H_{18}N_2O_3S$: C 66.65, H 4.79, N 7.40; Found: C 66.35, H 5.02, N 6.86.

Example 71

2-(4-methylsulfonylphenyl)-3-(4-fluorophenyl) indole

The procedure was in the same manner as described in example 59, except that the starting material was 2-N-(4-aminosulfonylbenzoyl)-amide-4'-fluoro-benzophenone prepared in Example 35 instead of 2-N-(4-methylsulfonylbenzoyl)-amide-benzophenone. The title compound was obtained as white crystal, yield 75.3%, m.p. 224–226° C. The data of Nuclear Magnetic Resonance shown that: $^1$HNMR (300 MHz, DMSO)δ: 3.24 (s, 3H, $SO_2CH_3$), 7.04–7.91 (m, 12H, Ar—H), 11.77 (s, 1H, N—H); Anal. Calcd for: $C_{21}H_{16}NFO_2S$: C 69.02, H 4.41, N 3.83; Found: C 69.19, H 4.56, N 4.00.

Example 72

2-(4-aminosulfonylphenyl)-3-(4-Fluorophenyl) indole

The procedure was in the same manner as described in example 59, except that the starting material was 2-N-(4-methylsulfonylbenzoyl)-amide-4'-fluoro-benzophenone prepared in Example 36 instead of 2-N-(4-methylsulfonylbenzoyl)-amide-benzophenone. The title compound was obtained as white crystal, yield 54.3%, m.p. 228–230° C. Analysis via Nuclear Magnetic Resonance provided the following information: $^1$HNMR (300 MHz, DMSO)δ: 3.33 (s, 2H, $SO_2NH_2$), 7.04–7.80 (m, 1 2H, Ar—H), 11.71 (s, 1H, N—H); Anal. Calcd for: $C_{20}H_{15}N_2FO_2S$: C 65.56, H 4.13, N 7.65; Found: C 65.46, H 4.23, N 7.35.

Example 73

2-(4-methylsulfonylphenyl)-3-(4-chlorophenyl)-5-chloroindole

The procedure was in the same manner as described in example 59, except that the starting material was 2-N-(4-methylsulfonylbenzoyl)-amide-5-chloro-4'-chloro-benzophenone prepared in Example 37 instead of 2-N-(4-methylsulfonylbenzoyl)-amide-benzophenone. The title compound was obtained as white crystal, yield 76.9%, m.p. 281–283° C. The data of Nuclear Magnetic Resonance shown that: $^1$HNMR (300 MHz, DMSO)δ:3.26 (s, 3H, $SO_2CH_3$), 7.22–7.95 (m, 11H, Ar—H), 12.06 (s, 1H, N—H); Anal. Calcd for: $C_{21}H_{15}NO_2SCl_2$: C 60.58, H 3.63, N 3.36; Found: C 60.72, H 3.79, N 3.30.

Example 74

2-(4-aminosulfonylphenyl)-3-(4-chlorophenyl)-5-chloroindole

The procedure was in the same manner as described in example 59, except that the starting material was 2-N-(4-aminosulfonylbenzoyl)-amide-5-chloro-4'-chloro-benzophenone prepared in Example 38 instead of 2-N-(4-methylsulfonylbenzoyl)-amide-benzophenone. The title compound was obtained as white crystal, yield 71.8%, m.p. 245–247° C. The data of Nuclear Magnetic Resonance shown that: $^1$HNMR (300 MHz, DMSO)δ:7.20–7.83 (m, 11H, Ar—H), 12.00 (s, 1H, N—H); Anal. Calcd for: $C_{20}H_{14}N_2O_2SCl_2$: C 57.56, H 3.38, N 6.71; Found: C 57.65, H 3.34, N 6.56.

Example 75

2-(4-aminosulfonylphenyl)-3-phenyl-5-chloroindole

The procedure was in the same manner as described in example 59, except that the starting material was 2-N-(4-aminosulfonylbenzoyl)-amide-5-chloro-benzophenone prepared in Example 39 instead of 2-N-(4-methylsulfonylbenzoyl)-amide-benzophenone. The title compound was obtained as white crystal, yield 27.5%, m.p. 297–299° C. The data of Nuclear Magnetic Resonance shown that: $^1$HNMR (300 MHz, DMSO) δ:3.32 (s, 2H, $SO_2NH_2$), 7.18–7.79 (m, 12H, Ar—H), 11.94 (s, 1H, N—H); Anal. Calcd for: $C_{20}H_{15}ClN_2O_2S$: C 62.74, H 3.95, N 7.32; Found: C 62.59, H 4.08, N 7.30.

Example 76

2-(4-methylsulfonylphenyl)-3-phenyl-5-chloroindole

The procedure was in the same manner as described in example 59, except that the starting material was 2-N-(4-methylsulfonylbenzoyl)-amide-5-chloro-benzophenone prepared in Example 40 instead of 2-N-(4-methylsulfonylbenzoyl)-amide-benzophenone. The title compound was obtained as white crystal, yield 84.3%, m.p. 281–283° C. Analysis via Nuclear Magnetic Resonance provided the following information: $^1$HNMR (300 MHz, DMSO)δ:3.24 (s, 3H, $SO_2CH_3$), 7.20–7.91 (m, 12H, Ar—H), 12.00 (s, 1H, N—H); Anal. Calcd for: $C_{21}H_{16}ClNO_2S$: C 66.05, H 4.22, N 3.67; Found: C 66.1 1, H 4.04, N 3.91.

Example 77

2-(4-aminosulfonylphenyl)-3-(2-chlorophenyl) -5-chloro indole

The procedure was in the same manner as described in example 59, except that the starting material was 2-N-(4-aminosulfonylbenzoyl)-amino-5-chloro-2'-chloro-benzophenone prepared in Example 41 instead of 2-N-(4-methylsulfonylbenzoyl)-amide-benzophenone. The title compound was obtained as white crystal, yield 47.6%, m.p. 268–240° C. The data of Nuclear Magnetic Resonance shown that: $^1$HNMR (300 MHz, DMSO)δ:3.28 (s, 2H, $SO_2NH_2$), 7.10–7.77 (m, 11H, Ar—H), 12.01 (s, 1H, N—H); Anal. Calcd for: $C_{20}H_{14}N_2O_2SCl$:$_2$C 57.56, H 3.38, N 6.71; Found: C 57.30, H 3.48, N 6.15.

Example 78

2-(4-methylsulfonylphenyl)-3-(2-chlorophenyl) -5-chloro indole

The procedure was in the same manner as described in example 59, except that the starting material was 2-N-(4-methylsulfonylbenzoyl)-amino-5-chloro-2'-chloro-benzophenone prepared in Example 42 instead of 2-N-(4-methylsulfonylbenzoyl)-amide-benzophenone. The title compound was obtained as white crystal, yield 70.2%, m.p. 300–301.5° C. The data of Nuclear Magnetic Resonance shown that: $^1$HNMR (300 MHz, DMSO)δ:3.23 (s, 3H, $SO_2CH_3$), 7.10–7.91 (m, 11H, Ar—H), 12.13 (s, 1H, N—H); Anal. Calcd for: $C_{21}H_{15}NO_2SCl_2$: C 57.56, H 3.38, N 3.36; Found: C 60.59, H 3.62, N 3.40.

Example 79

2-(4-methylsulfonylphenyl)-3-phenyl-5-fluoroindole

The procedure was in the same manner as described in example 59, except that the starting material is 2-N-(4-methylsulfonylbenzoyl)-amide-5-fuoro-benzophenone prepared in Example 43 instead of 2-N-(4-methylsulfonylbenzoyl)-amide-benzophenone. The title compound was obtained as white crystal, yield 79.8%, m.p. 243–245° C. The data of Nuclear Magnetic Resonance shown that: $^1$HNMR (300 MHz, DMSO)δ:3.24 (s, 3H, $SO_2CH_3$), 7.02–7.91 (m, 12H, Ar—H), 11.89 (s, 1H, N—H); Anal. Calcd for: $C_{21}H_{16}NFO_2S$: C 69.02, H 3.83, N 4.41; Found: C 69.18, H 4.34, N 3.65.

Example 80

2-(4-aminosulfonylphenyl)-3-phenyl-5-fluoroindole

The procedure was in the same manner as described in example 59, except that the starting material was 2-N-(4-aminosulfonylbenzoyl)-amide-5-fuoro-benzophenone prepared in Example 44 instead of 2-N-(4-methylsulfonylbenzoyl)-amide-benzophenone. The title compound was obtained as white crystal, yield 59.3%, m.p. 302–304° C. The data of Nuclear Magnetic Resonance shown that: $^1$HNMR (300 MHz, DMSO)δ:3.35 (s, 2H, $SO_2NH_2$), 7.01–7.79 (m, 12H, Ar—H), 11.82 (s, 1H, N—H); Anal. Calcd for: $C_{20}H_{15}N_2FO_2S$: C 65.56, H 4.13, N 7.65; Found: C 65.46, H 4.16, N 7.43.

Example 81

2-(4-aminosulfonylphenyl)-3-phenyl-5-bromoindole

The procedure was in the same manner as described in example 59, the starting material was 2-N-(4-aminosulfonylbenzoyl)-amide-5-bromo-benzophenone prepared in Example 45 instead of 2-N-(4-methylsulfonylbenzoyl)-amide-benzophenone. The title compound was obtained as white crystal, yield 55.3%, m.p. 310–312° C.; $^1$HNMR (300 MHz, DMSO)δ:3.31 (s, 2H, $SO_2NH_2$), 7.29–7.78 (m, 12H, Ar—H), 11.94 (s, 1H, N—H); Anal. Calcd for: $C_{20}H_{15}N_2O_2SBr$: C 56.23, H 3.54, N 6.56; Found: C 56.45, H 3.76, N 6.60.

Example 82

2-(4-methylsulfonylphenyl)-3-phenyl-5-bromoindole

The procedure is in the same manner as described in example 59, except that the starting material is 2-N-(4-methylsulfonylbenzoyl)-amide-5-bromo-benzophenone prepared in Example 46 instead of 2-N-(4-methylsulfonylbenzoyl)-amide-benzophenone. The title compound was obtained as white crystal, yield 69.1%, m.p. 262–264° C. The data of Nuclear Magnetic Resonance shown that: $^1$HNMR (300 MHz, DMSO)δ: 3.23 (s, 3H, $SO_2CH_3$), 7.30–7.90 (m, 12H, Ar—H), 12.01 (s, 1H, N—H); Anal. Calcd for: $C_{21}H_{16}NO_2SBr$: C 59.17, H 3.78, N 3.29; Found: C 59.11, H 3.71, N 3.44.

Example 83

2-(4-methylsulfonylphenyl)-3-phenyl-5-methylindole

The procedure was in the same manner as described in example 59, except that the starting material was 2-N-(4-methylsulfonylbenzoyl)-amide-5-methyl-benzophenone prepared in Example 47 instead of 2-N-(4-methylsulfonylbenzoyl)-amide-benzophenone. The title compound was obtained as white crystal, yield 71.8%, m.p. 245–247° C. The data of Nuclear Magnetic Resonance shown that: $^1$HNMR (300 MHz, DMSO)δ:7.20–7.83 (m, 11H, Ar—H), 12.00 (s, 1H, N—H); Anal. Calcd for: $C_{20}H_{14}N_2O_2SCl_2$: C 57.56, H 3.38, N 6.71; Found: C 57.65, H 3.34, N 6.56.

Example 84

2-(4-aminosulfonylphenyl)-3-phenyl-5-methylindole

The procedure was in the same manner as described in example 59, except that the starting material was 2-N-(4-aminosulfonylbenzoyl)-amide-5-methyl-benzophenone prepared in Example 48 instead of 2-N-(4-methylsulfonylbenzoyl)-amide-benzophenone. The title compound was obtained as white crystal, yield 76.2%, m.p. 242–244° C. The data of Nuclear Magnetic Resonance shown that: $^1$HNMR (300 MHz, DMSO)δ:2.36 (s, 3H, $CH_3$), 3.32 (s, 2H, $SO_2NH_2$), 7.01–7.77 (m, 12H, Ar—H), 11.57 (s, 1H, N—H); Anal. Calcd for: $C_{21}H_{18}N_2O_2S$: C 69.59, H 5.01, N 7.73; Found: C 69.78, H 4.95, N 7.71.

Example 85

2-(4-aminosulfonylphenyl)-3-(3-chlorophenyl)-5-chloroindole

The procedure was in the same manner as described in example 59, except that the starting material was 2-N-(4-aminosulfonylbenzoyl)-amide-5-chloro-3'-chloro-benzophenone prepared in Example 49 instead of 2-N-(4-methylsulfonylbenzoyl)-amide-benzophenone. The title compound was obtained as white crystal, yield 68.2%, m.p. 249–251° C. The data of Nuclear Magnetic Resonance shown that: $^1$HNMR (300 MHz, DMSO)δ: 3.27 (s, 2H, $SO_2NH_2$), 7.21–7.84 (m, 11H, Ar—H), 12.00 (s,1H, N—H); Anal. Calcd for: $C_{20}H_{14}NO_2SCl$: C 57.56, H 3.38, N 6.71; Found: C 57.53, H 3.44, N 6.43.

Example 86

2-(4-methylsulfonylphenyl)-3-(3-chlorophenyl)-5-chloroindole

The procedure was in the same manner as described in example 59, except that the starting material was 2-N-(4- methylsulfonylbenzoyl)-amide-5-chloro-3'-chloro-benzophenone prepared in Example 50 instead of 2-N-(4-methylsulfonylbenzoyl)-amide-benzophenone. The title compound was obtained as white crystal, yield 56.0%, m.p. 254–257° C. The data of Nuclear Magnetic Resonance shown that: $^{1}$HNMR (300 MHz, DMSO)δ:3.26 (s, 3H, $SO_2CH_3$), 7.22–7.96 (m, 11H, Ar—H), 12.10 (s, 1H, N—H); Anal. Calcd for: $C_{21}H_{15}NO_2SCl_2$: C 60.58, H 3.63, N 3.36; Found: C 60.56, H 3.75, N 3.34.

Example 87

2-phenyl-3-(4-methylsulfonylphenyl)-5-chloroindole

The procedure was in the same manner as described in example 59, except that the starting material was 2-N-(4-benzoyl)-amide-5-chloro-4'-methylsulfonyl-benzophenone prepared in Example 51 instead of 2-N-(4-methylsulfonylbenzoyl)-amide-benzophenone. The title compound was obtained as white crystal, yield 54.2%, m.p. 273–275° C. The data of Nuclear Magnetic Resonance shown that: $^{1}$HNMR (300 MHz, DMSO)δ:3.25 (s, 3H, $SO_2CH_3$), 7.20–7.94 (m, 12H, Ar—H), 12.05 (s, 1H, N—H); Anal. Calcd for: $C_{21}H_{16}NO_2SCl$: C 66.05, H 4.22, N 3.67; Found: C 65.98, H 4.47, N 3.75

Example 88

2-(4-methylsulfonylphenyl)-3-(4-methylsulfonylphenyl)-5-chloroindole

The procedure was in the same manner as described in example 59, except that the starting material was 2-N-(4-methylsulfonylbenzoyl)-amide-5-chloro-4'-methylsulfonyl-benzophenone prepared in Example 52 instead of 2-N-(4-methylsulfonylbenzoyl)-amide-benzophenone. The title compound was obtained as white crystal, yield 46.8%, m.p. 173–175° C. The data of Nuclear Magnetic Resonance shown that: $^{1}$HNMR (300 MHz, DMSO)δ:3.25 (s, 3H, $SO_2CH_3$), 3.27 (s, 3H, $SO_2CH_3$), 7.23–7.96 (m, 11H, Ar—H), 12.16 (s, 1H, N—H); Anal. Calcd for: $C_{22}H_{18}NO_4S_2Cl$: C 57.45, H 3.94, N 3.05; Found: C 57.74, H 4.30, N 73.10.

Example 89

2-(4-chlorophenyl)-3-(4-methylsulfonylphenyl)-5-chloroindole

The procedure was in the same manner as described in example 59, except that the starting material was 2-N-(4-chlorobenzoyl)-amide-5-chloro-4'-methylsulfonyl-benzophenone prepared in Example 53 instead of 2-N-(4-methylsulfonylbenzoyl)-amide-benzophenone. The title compound was obtained as white crystal, yield 79.9%, m.p. 269–271° C. The data of Nuclear Magnetic Resonance shown that: $^{1}$HNMR (300 MHz, DMSO)δ:3.25 (s, 3H, $SO_2CH_3$), 7.20–7.94 (m, 11H, Ar—H), 12.05 (s, 1H, N—H); Anal. Calcd for: $C_{21}H_{15}NO_2SCl_2$: C 60.58, H 3.63, N 3.36; Found: C 60.58, H 3.68, N 3.07.

Example 90

2-(4-methoxyphenyl)-3-(4-methylsulfonylphenyl)-5-chloroindole

The procedure was in the same manner as described in example 59, except that the starting material was 2-N-(4-methoxybenzoyl)-amide-5-chloro-4'-methylsulfonyl-benzophenone prepared in Example 54 instead of 2-N-(4-methylsulfonylbenzoyl)-amide-benzophenone. The title compound was obtained as white crystal, yield 66.6%, m.p. 246–248° C. The data of Nuclear Magnetic Resonance shown that: $^{1}$HNMR (300 MHz, DMSO)δ:3.23 (s, 3H, $SO_2CH_3$), 3.74 (s, 3H, $CH_3$), 6.97–7.92 (m, 11H, Ar—H), 11.87 (s, 1H, N—H); Anal. Calcd for: $C_{22}H_{18}NO_3SCl$: C 64.15, H 4.40, N 3.40; Found: C 63.93, H 4.40, N 3.13.

Example 91

2-(4-methylphenyl)-3-(4-methylsulfonylphenyl)-5-chloroindole

The procedure was in the same manner as described in example 59, except that the starting material was 2-N-(4-methylbenzoyl)-amide-5-chloro-4'-methylsulfonyl-benzophenone prepared in Example 55 instead of 2-N-(4-methylsulfonylbenzoyl)-amide-benzophenone. The title compound was obtained as white crystal, yield 69.2%, m.p. 238–240° C. Analysis via Nuclear Magnetic Resonance provided the following information: $^{1}$HNMR (300 MHz, DMSO)δ: 2.32 (s, 3H, $CH_3$), 3.24 (s, 3H, $SO_2CH_3$), 7.16–7.92 (m, 11H, Ar—H), 11.92 (s, 1H, N—H); Anal. Calcd for: $C_{22}H_{18}NO_2SCl$: C 66.74, H 4.58, N 3.54; Found: C 66.81, H 4.58, N 3.54.

Example 92

2-(2-fluorophenyl)-3-(4-methylsulfonylphenyl)-5-chloroindole

The procedure was in the same manner as described in example 59, except that the starting material is prepared in Example 56 instead of 2-N-(4-methylsulfonylbenzoyl)-amide-benzophenone. The title compound was obtained as white crystal, yield 60.0%, m.p. 246–248° C. The data of Nuclear Magnetic Resonance shown that: $^{1}$HNMR (300 MHz, DMSO)δ:3.21 (s, 3H, $SO_2CH_3$), 7.21–7.88 (m, 11H, Ar—H), 12.04 (s, 1H, N—H); Anal. Calcd for: $C_{21}H_{15}FNO_2SCl$: C 63.07, H 3.78, N 3.50; Found: C 63.30, H 3.93, N 3.27.

Example 93

2-(2-acetyloxyphenyl)-3-(4-methylsulfonylphenyl)-5-chloroindole

The procedure was in the same manner as described in example 59, except that the starting material was 2-N-(2-acetyloxylbenzoyl)-amide-5-chloro-4'-methylsulfonyl-benzophenone prepared in Example 57 instead of 2-N-(4-methylsulfonylbenzoyl)-amide-benzophenone. The title compound was obtained as white crystal, yield 67.0%, m.p. 238–240° C. The data of Nuclear Magnetic Resonance shown that: $^{1}$HNMR (300 MHz, DMSO)δ:1.85 (s, 3H, $CH_3$), 3.20 (s, 3H, $SO_2CH_3$), 7.19–7.86 (m, 11H, Ar—H), 11.93 (s, 1H, N—H); Anal. Calcd for: $C_{23}H_{18}NO_4SCl$: C 62.80, H 4.12, N 3.18; Found: C 62.56, H 4.31, N 2.82.

Example 94

2-(4-acetyloxyphenyl)-3-(4-methylsulfonylphenyl)-5-chloroindole

The procedure was in the same manner as described in example 59, except that the starting material was 2-N-(4-acetyloxylbenzoyl)-amide-5-chloro-4'-methylsulfonyl-benzophenone prepared in Example 58 instead of 2-N-(4-methylsulfonylbenzoyl)-amide-benzophenone. The title compound was obtained as white crystal, yield 70.0%, m.p.

248–250° C. The data of Nuclear Magnetic Resonance shown that: $^1$HNMR (300 MHz, DMSO)δ:2.28 (s, 3H, $CH_3$), 3.26 (s, 3H, $SO_2CH_3$), 7.19–7.95 (m, 11H, Ar—H), 12.02 (s, 1H, N—H); Anal. Calcd for: $C_{23}H_{18}NO_4SCl$: C 62.80, H 4.12, N 3.18; Found: C 62.83, H 4.08, N 2.96.

Example 95

2-(4-hydroxyphenyl)-3-(4-methylsulfonylphenyl)-5-chloroindole

To a solution 150 mg (0.34 m mol) of 2-(4-acetyloxylphenyl)-3-(4-methylsulfonylphenyl)-5-chloroindole prepared in Example 94 in 10 ml of THF was added the solution of 20 mg of NaOH in 10 ml of 95% ethanol. The reaction mixture was stirred at room temperature for 4 h, and the solvent was removed. To the residue 10 ml of 0.5N HCl was added and the resulting precipiptate was filtered off, washed with water, dried, recrystallized from 95% ethanol to afford 123 mg of the title compound as white needle crystal, yield 90.7%, m.p. 271–273° C. Analysis via Nuclear Magnetic Resonance provided the following information: $^1$HNMR (300 MHz, DMSO)δ:3.23 (s, 3H, $SO_2CH_3$), 6.78–7.92 (m, 11H, Ar—H), 9.78 (s, 1H, OH), 11.83 (s, 1H, N—H); Anal. Calcd for: $C_{21}H_{16}NO_3SCl$: C 63.39, H 4.05, N 3.52; Found: C 63.31, H 4.24, N 3.51.

Example 96

2-(4-aminosulfonylphenyl)-3-(4-hydroxyphenyl)indole 300 mg (0.79 m mol) of 2-(4-aminosulfonylphenyl)-3-(4-methoxyphenyl)indole prepared in Example 70 was suspended in 20 ml of CH2Cl2 cooled in an ice-salt bath and the cold solution of 0.41 ml (4.4 m mol) of BBR3 in 5 ml of CH2Cl2 was added in dropwise. When addition was complete, the ice-salt bath was removed and the reaction mixture was stirred at room temperature for 3 h. The solvent was removed and the residue was purified by column chromtography eluting with 3:1 petroleum: ethyl acetate to give 180 mg of title compound as light yellow crystal, yield 62.31%, m.p. 241–243° C. The data of Nuclear Magnetic Resonance shown that: $^1$HNMR (300 MHz, DMSO) δ:6.80–7.77 (m, 11H, Ar—H), 9.43 (s, 1H, OH), 11.56 (s, 1H, N—H); Anal. Calcd for: $C_{20}H_{16}N_2O_3S$: C 56.92, H 4.43, N 7.69; Found: C 56.81, H 4.34, N 7.47.

Example 97

2-(N-acetamide-sulfonylphenyl)-3-phenylindole

To a solution of 1.5 g (4.3 m mol) of 2-(4-aminosulfonylphenyl)-3-phenylindole prepared in Example 60, 5 mg of DMAP, and 0.5 g (5.2 m mol) of triethylamine in 20 ml dry THF was added dropwise 0.5 g (5.2 m mol) of acetic anhydride. The reaction mixture was stirred at room temperature for 5 h and then the solvent was removed in vacuo. The residue was crystallized from dichloromethane to afford 1.0 g of the title compound as needle yellow crystal, yield 59.30%, m.p. 221–222° C. The data of Nuclear Magnetic Resonance shown that: $^1$HNMR (300 MHz, DMSO)δ:1.92 (s, 3H, $CH_3$), 7.05–7.86 (m, 13H, Ar—H), 11.69 (s, 1H, N—H), 12.04 (s, 1H, N—H); Anal. Calcd for: $C_{22}H_{18}N_2O_3S$: C 67.67, H 4.65, N 7.17; Found: C 67.79, H 4.68, N 7.08.

Method B

Example 98

4-methylsulfonylphenylacetonphenone

A mixture of 5.0 g (0.023 mol) of 4-methylsulfonylphenacetic acid and 10 ml of thionyl chloride were heated under reflux to give a clear solution. Removal of the excess of thionyl chloride under reduced pressure to give a light yellow solid and without purification put into the next reaction. To the solution of the solid obtained above in 30 ml of dry benzene was added in portions 4.7 g (0.035 mol) of anhydrous aluminum chloride at 20–25° C. When addition was complete, the mixture was heated to reflux for 2 h, then cooled and poured into a mixture of ice and 10 ml of 1N hydrochloride acid. The benzene was removed in vacuo and the crude product was separated by filtration and washed with sodium carbonate and water. The filter cake is sucked reasonably dry and recrystallized from 95% ethanol to give 3.9 g of the title compound as light yellow crystal, yield 60.9%, m.p. 190–192° C.

Example 99

4-aminolsulfonylphenyl-acetophenone

The procedure was in the same manner as described in example 97, except that the starting material was 4-aminosulfonylphenylacetic acid instead of 4-Methylsulfonylphenylacetic acid The title compound was obtained as light yellow needle crystal, yield 20.5%, m.p. 209–212.

Example 100

2- phenyl-3-(4-methylsulfonylphenyl)indole

The mixture of 0.9 g (3.3 m mol) of 4-methylsulfonylphenyl-actophenone prepared in Example 97 and 0.5 g (3.3m mol) of phenylhydrazine hydrochloride were heated at 130° C. for 0.5 h. After cooling, 20 ml of acetic acid and 0.2 g of BF3.Et2O was added and heated to reflux for 1 h. Acetic acid was removed in vacuo, the resulting residue was suspended in water, filtered, dried and purified by column chromatography using petroleum ether/ethyl acetate 3:1 as elutant, 0.45 g of the title compound was obtained as white crystal, yield, 39.5%, m.p. 239–241° C. The data of Nuclear Magnetic Resonance shown that: $^1$HNMR (300 MHz, DMSO)δ: 3.24 (s, 3H, $SO_2CH_3$), 7.05–7.90 (m, 13H, Ar—H), 11.77 (s, 1H, N—H); Anal. Calcd for: $C_{21}H_{17}NO_2S$: C 72.60, H 4.93, N 4.03; Found: C 72.35, H 5.03, N 4.25.

Example 101

2-phenyl-3-(4-aminosulfonylphenyl)indole

The procedure was in the same manner as described in example 99, except that the starting material was 4-aminolsulfonylphenyl-acetophenone prepared in Example 98 instead of 4-methylsulfonylphenyl acetophenone. The title compound was obtained as light yellow needle crystal, yield 29.5%, m.p. 223–225° C. Analysis via Nuclear Magnetic Resonance provided the following information:

$^1$HNMR (300 MHz, DMSO)δ: 3.32 (s, 2H, $SO_2NH_2$), 7.04–7.82 (m, 13H, Ar—H), 11.71 (s, 1H, N—H); Anal. Calcd for: $C_{20}H_{16}N_2O_2S$: C 68.94, H 4.63, N 8.04; Found: C 68.95, H 4.71, N 7.78.

Pharmacological Effects

1. In vitro Test of Inhibitory Activity for Cyclooxygenase-2 and Cyclooxygenase-1

Cell culture: Adherent macrophages were harvested from the peritoneal cells of male mice (C57BL-6J, Level 2, from Experiment Animal Center, Academy of Military Medical Science) 3 d after the injection (ip) of brewer thioglycollate medium (5 mL/100 g body weight). Shortly, peritoneal cells obtained from 3~4 mice were mixed and seeded in 48 well cell culture cluster (Costar) at a cell density of $1\times10^9$ cell/L in RPMI-1640 supplemented with 5% (v/v) newborn calf serum, 100 ku/L penicillin and 100 g/L streptomycin. After settlement for 2~3 h, non-adherent cells were washed by D-Hanks' balanced salt solution. Then macrophages were cultured in RPMI-1640 without serum. Almost all of adherent cells were macrophages as assessed by Giemsa staining. Cell viability was examined by trypan blue dye exclusion. All incubation procedures were performed with 5% $CO_2$ in humidified air at 37° C.

COX-2 assay: Macrophages were incubated with test compound at different concentrations or solvent ($Me_2SO$) for 1 h and were stimulated with LPS 1 mg/L for 9 h. The amount of $PGE_2$ in supernatants was measured by RIA. The inhibitory ratio was calculated using the same Formula as in COX-1 assay section. Cs, Ct, Cc refer to $PGE_2$ concentration in supernatants of LPS, test compound, and control groups, respectively.

COX-1 assay: Macrophages were incubated with test compound at different concentrations or solvent ($Me_2SO$) for 1 h and were stimulated with calcimycin 1 $\mu mol\cdot L^{-1}$ for 1 h. The amount of 6-keto-$PGF_1$ (a stable metabolite of $PGI_2$) in supernatants was measured by RIA according to manufacturer's guide. The inhibitory ratio was calculated as $$IR = \frac{(Cs - Ct)}{(Cs - Cc)}$$

Cs, Ct, Cc refer to 6-keto-$PGF_1$ concentration in supernatants of calcimycin, test compound, and control groups, respectively.

Statistical analysis: Data were expressed as the mean±SD of more than three independent experiments. Dose-inhibitory effect curves were fit through "uphill dose response curves, variable slope" using Prism, GraphPad (version 3.00):

$$Y = \frac{1}{1 + 10^{[(logIC_{50} - X) \times Hillslope]}}$$

The inhibitory activities of the compounds of present invention for COX-2 and COX-1 in cell culture are listed in TABLE 1

TABLE 1

Inhibitory activity for COX-2 and COX-1

| Example No | $IC_{50}$ COX-2 (M) | $IC_{50}$ COX-1 ($OD_{611}$) |
|---|---|---|
| 59 | $3.86 \times 10^{-9}$ | 0.24 |
| 60 | $1.61 \times 10^{-10}$ | 0.19 |
| 61 | $1.46 \times 10^{-7}$ | 0.17 |

TABLE 1-continued

Inhibitory activity for COX-2 and COX-1

| Example No | $IC_{50}$ COX-2 (M) | $IC_{50}$ COX-1 ($OD_{611}$) |
|---|---|---|
| 62 | $3.35 \times 10^{-8}$ | 0.09 |
| 63 | $3.69 \times 10^{-10}$ | 0.18 |
| 64 | $8.36 \times 10^{-9}$ | 0.07 |
| 65 | $8.96 \times 10^{-11}$ | 0.14 |
| 66 | $6.84 \times 10^{-11}$ | 0.08 |
| 67 | $1.66 \times 10^{-10}$ | 0.14 |
| 68 | $1.46 \times 10^{-9}$ | 0.07 |
| 69 | $2.20 \times 10^{-11}$ | 0.11 |
| 70 | $6.70 \times 10^{-12}$ | 0.08 |
| 71 | $2.35 \times 10^{-11}$ | 0.15 |
| 72 | $5.15 \times 10^{-9}$ | 0.12 |
| 73 | $8.51 \times 10^{-8}$ | 0.18 |
| 74 | $5.41 \times 10^{-10}$ | 0.11 |
| 75 | $1.43 \times 10^{-10}$ | 0.08 |
| 76 | $3.59 \times 10^{-10}$ | 0.27 |
| 77 | $1.0 \times 10^{-7}$ | 0.14 |
| 78 | $1.0 \times 10^{-8}$ | 0.27 |
| 79 | $5.0 \times 10^{-9}$ | 0.13 |
| 80 | $2.0 \times 10^{-9}$ | 0.08 |
| 81 | $5.0 \times 10^{-9}$ | 0.09 |
| 82 | $1.41 \times 10^{-9}$ | 0.20 |
| 83 | $2.78 \times 10^{-10}$ | 0.22 |
| 84 | $1.71 \times 10^{-11}$ | 0.15 |
| 85 | $3.13 \times 10^{-9}$ | 0.14 |
| 86 | $8.01 \times 10^{-10}$ | 0.18 |
| 87 | $2.7 \times 10^{-10}$ | 0.23 |
| 88 | $1.48 \times 10^{-9}$ | 0.23 |
| 89 | $3.54 \times 10^{-7}$ | 0.27 |
| 90 | $2.81 \times 10^{-9}$ | 0.22 |
| 91 | $1.68 \times 10^{-9}$ | 0.27 |
| 92 | $1.76 \times 10^{-9}$ | 0.23 |
| 93 | $6.0 \times 10^{-9}$ | 0.22 |
| 94 | $7.16 \times 10^{-9}$ | 0.16 |
| 95 | n.d. | n.d. |
| 96 | $6.44 \times 10^{-9}$ | 0.19 |
| 97 | $1.84 \times 10^{-10}$ | 0.25 |
| 100 | $2.16 \times 10^{-10}$ | 0.16 |
| 101 | $2.55 \times 10^{-9}$ | 0.22 |
| Celecoxib | $5.15 \times 10^{-10}$ | 0.11 |

In vitro Test of Inhibitory Activity for Cyclooxygenase-1 Rat Carrageenan-induced Foot Pad Edema Assay Male Sprgue-Dawley rats (190–220 g ) were fasted with free access to water at least 16 h prior experiments. The rats were dosed orally with a 1 ml suspension of test compound in vehicle (0.5% methyl cellulose and 0.025% Tween-20) or with vehicle alone. One hour later a subplantar injection of 0.1 ml of 1% solution of carageenan in 0.9% strile saline was administered to the right hind foot pad. Paw volume was measured with a displacement plethysmometer 2, 3, and 4 h after carrageenan injection. The results are listed in TABLE 2.

TABLE 2

Inhibition of rat carrageenan-induced foot pad edema

| Example | Dosage | Paw volume and inhibitory percentage of edema(%) hr | | |
|---|---|---|---|---|
| No | (mg/kg) | 2 | 3 | 4 |
| Contrast | 10 | 41.5 ± 8.3 | 62.6 ± 14.0 | 51.9 ± 17.9 |
| 61 | 10 | 14.6 ± 7.8 | 30.6 ± 10.0 (51.1) | 25.7 ± 10.1 (50.4) |
| 62 | 10 | 16.6 ± 6.5 | 41.3 ± 13.7 (24.2) | 38.6 ± 14.9 (25.6) |

TABLE 2-continued

| Inhibition of rat carrageenan-induced foot pad edema | | | | |
|---|---|---|---|---|
| Example | Dosage | Paw volume and inhibitory percentage of edema(%) hr | | |
| No | (mg/kg) | 2 | 3 | 4 |
| 63 | 10 | 27.1 ± 10.1 | 55.3 ± 17.0 (11.6) | 43.6 ± 9.5 (16.1) |
| 65 | 10 | 18.5 ± 8.1 | 35.8 ± 6.8 (42.8) | 27.4 ± 7.1 (47.2) |
| 67 | 10 | 25.6 ± 13.4 | 43.9 ± 11.0 (29.8) | 29.5 ± 12.0 (43.1) |
| 69 | 10 | 21.6 ± 12.4 | 43.4 ± 12.1 (30.6) | 37.8 ± 10.7 (27.1) |
| 70 | 10 | 21.9 ± 11.8 | 34.6 ± 10.4 (44.7) | 31.9 ± 11.9 (38.5) |
| 71 | 10 | 44.0 ± 21.1 | 54.4 ± 9.8 (11.1) | 49.1 ± 19.0 (18.4) |
| 72 | 10 | 32.8 ± 13.2 | 36.4 ± 16.9 (40.5) | 35.4 ± 11.3 (41.2) |
| 87 | 10 | 45.4 ± 9.7 | 46.9 ± 13.6 (23.4) | 43.4 ± 13.4 (27.9) |
| 89 | 10 | 58.6 ± 15.8 | 66.5 ± 13.4 (46.1) | 58.4 ± 13.8 (29.9) |
| 101 | 10 | 36.6 ± 8.9 | 39.1 ± 15.4 (36.1) | 33.6 ± 16.5 (44.2) |
| 59 | 10 | 40.8 ± 15.8 | 48.6 ± 14.0 (55.8) | 41.2 ± 17.4 (56.1) |
| 60 | 10 | 32.5 ± 9.45 | 56.9 ± 16.4 (48.3) | 43.2 ± 13.9 (53.9) |
| 75 | 10 | 35.6 ± 25.5 (50.1) | 44.1 ± 31.4 (54.8) | 34.0 ± 13.6 (57.8) |
| 76 | 10 | 45.0 ± 17.9 (36.9) | 46.0 ± 15.4 (52.8) | 37.7 ± 15.6 (53.2) |
| 79 | 10 | 41.8 ± 7.2 (41.4) | 47.7 ± 15.8 (51.5) | 31.6 ± 13.3 (60.8) |
| 80 | 10 | 36.7 ± 7.4 (48.6) | 46.6 ± 14.0 (52.2) | 40.8 ± 17.6 (49.4) |
| 83 | 10 | 35.1 ± 17.5 (46.1) | 51.6 ± 17.9 (47.1) | 43.4 ± 18.4 (46.1) |
| 84 | 10 | 63.1 ± 18.1 (40.5) | 65.6 ± 15.4 (32.8) | 62.4 ± 15.7 (22.6) |
| 85 | 10 | 57.2 ± 13.6 (19.8) | 62.3 ± 7.2 (36.1) | 61.7 ± 8.8 (23.4) |
| 90 | 10 | 44.2 ± 11.9 (38.1) | 46.5 ± 5.7 (52.4) | 40.8 ± 5.3 (49.6) |
| 92 | 10 | 31.3 ± 17 (56.2) | 44.6 ± 13.7 (54.3) | 35.4 ± 18.8 (56.1) |
| 93 | 10 | 49.5 ± 8.2 (30.7) | 54.4 ± 8.9 (44.3) | 53.6 ± 11.4 (33.5) |
| 94 | 10 | 58.8 ± 11.4 (17.6) | 62.1 ± 7.1 (36.3) | 56.4 ± 11.7 (30.0) |
| 100 | 10 | 42.8 ± 15.1 (40.1) | 54.4 ± 7.9 (44.3) | 43.5 ± 8.9 (46.1) |
| Celecoxib | 10 | 31.1 ± 7.87 | 53.2 ± 12.6 (51.6) | 48.8 ± 8.11 (48.0) |
| Rofecoxib | 10 | 50.3 ± 5.1 (29.5) | 47.2 ± 2.4 (51.6) | 38.2 ± 6.7 (52.6) |

The above description is for the purpose of teaching a skilled artisan how to practice the invention, and it is not intended to detail all of those obvious modifications and variations of it which will become apparent to the skilled worker upon reading the description. It is intended, however, that all such obvious modifications and variations be included within the scope of the invention which is defined by the following claims. The claims are meant to cover the claimed elements and steps in any arrangement or sequence that is effective to meet the objectives there intended, unless the context specifically indicates the contrary. Those skilled in the art will recognize, or be able to ascertain using no more than routine experimentation, many equivalents to the specific embodiments of the invention specifically described herein. Such equivalents are intended to be encompassed in the scope of the following claims.

What is claimed is:

1. A compound of Formula I:

(I)

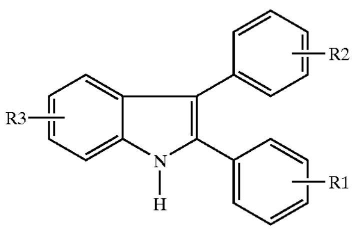

and pharmaceutically acceptable salts thereof, wherein $R_1$ is selected from the group consisting of 4-methylsulfonyl, 4-aminosulfonyl, cyano, amino and trifluoromethyl;

$R_2$ is selected from the group consisting of 4-methylsulfonyl, 4-aminosulfonyl, cyano, nitro, amino and trifluoromethyl; and $R_3$ is selected from the group consisting of 4-halogen, 5-halogen, 6-halogen or 7-halogen, nitro, and amino.

2. The compound defined in claim 1, wherein $R_1$ is selected from the group consisting of 4-methylsulfonyl, and 4-aminosulfonyl;

$R_2$ is selected from the group consisting of 4-methylsulfonyl- and 4-aminosulfonyl; and $R_3$ is 5-halogen.

3. The compound defined in claim 1, wherein $R_2$ is a 4-methylsulfonyl or 4-aminosulfonyl.

4. The compound defined in claim 1, wherein halogen is selected from the group consisting of F, Cl and Br.

5. The compound defined in claim 1, wherein the compound is 2-(4-methylsulfonylphenyl)-3-phenylindole and pharmaceutically acceptable salts thereof.

6. The compound defined in claim 1, wherein the compound is 2-(4-aminosulfonylphenyl)-3-phenylindole and pharmaceutically acceptable salts thereof.

7. The compound defined in claim 1, wherein the compound is 2-(4-methylsulfonylphenyl)-3-(4-chlorophenyl) indole and pharmaceutically acceptable salts thereof.

8. The compound defined in claim 1, wherein the compound is 2-(4-aminosulfonylphenyl)-3-(4-chlorophenyl) indole and pharmaceutically acceptable salts thereof.

9. The compound defined in claim 1, wherein the compound is 2-(4-methylsulfonylphenyl)-3-(4-chlorophenyl) indole and pharmaceutically acceptable salts thereof.

10. The compound defined in claim 1, wherein the compound is 2-(4-aminosulfonylphenyl)-3-(4-bromophenyl) indole and pharmaceutically acceptable salts thereof.

11. The compound defined in claim 1, wherein the compound is 2-(4-methylsulfonylphenyl)-3-(4-methylphenyl) indole and pharmaceutically acceptable salts thereof.

12. The compound defined in claim 1, wherein the compound is 2-(4-aminosulfonylphenyl)-3-(4-methylphenyl) indole and pharmaceutically acceptable salts thereof.

13. The compound defined in claim 1, wherein the compound is 2-(4-methylsulfonylphenyl )-3-(3,4-dimethylphenyl)indole and pharmaceutically acceptable salts thereof.

14. The compound defined in claim 1, wherein the compound is 2-(4-aminosulfonylphenyl)-3-(3,4-dimethylphenyl)indole and pharmaceutically acceptable salts thereof.

15. The compound defined in claim 1, wherein the compound is 2-(4-methylsulfonylphenyl)-3-(4-methoxyphenyl) indole and pharmaceutically acceptable salts thereof.

16. The compound defined in claim 1, wherein the compound is 2-(4-aminosulfonylphenyl)-3-(4-methoxyphenyl) indole and pharmaceutically acceptable salts thereof.

17. A pharmaceutical composition comprising a therapeutically effective amount of the compound defined in claim 1 and a pharmaceutically acceptable carrier.

18. A pharmaceutical composition comprising a therapeutically effective amount of the compound defined in claim 2 and a pharmaceutically acceptable carrier.

* * * * *

UNITED STATES PATENT AND TRADEMARK OFFICE

CERTIFICATE OF CORRECTION

PATENT NO. : 6,960,611 B2
APPLICATION NO. : 10/243957
DATED : November 1, 2005
INVENTOR(S) : Zongru Guo et al.

It is certified that error appears in the above-identified patent and that said Letters Patent is hereby corrected as shown below:

On The Title Page

Item
Delete "(73) Assignee: Institute of Materia Medica, Beijing (CN)"

and insert therefor

Item
--(73) Assignee: Institute of Materia Medica, Beijing (CN) and Jiangsu Hengrui Medicine Company, Ltd., Jiangsu Province (CN)--

Signed and Sealed this

Fourth Day of March, 2008

JON W. DUDAS
*Director of the United States Patent and Trademark Office*